United States Patent
Rackers et al.

(10) Patent No.: US 11,903,569 B2
(45) Date of Patent: Feb. 20, 2024

(54) BIOPSY SYSTEM WITH A CORE COLLECTOR THAT REMAINS RADIALLY CENTERED IN AN OUTER CANNULA WHILE SEVERING A TISSUE SAMPLE

(71) Applicant: URO-1, Inc., Winston-Salem, NC (US)

(72) Inventors: Kevin Rackers, Greensboro, NC (US); Philip Allred, Kernersville, NC (US); Jack Snoke, Winston Salem, NC (US); Rob Deckman, San Bruno, CA (US); Ted Belleza, LaSelva Beach, NC (US); Bela Denes, Jacksonville, OR (US)

(73) Assignee: URO-1, Inc., Winston-Salem, NC (US)

( * ) Notice: Subject to any disclaimer, the term of this patent is extended or adjusted under 35 U.S.C. 154(b) by 258 days.

(21) Appl. No.: 17/082,387

(22) Filed: Oct. 28, 2020

(65) Prior Publication Data

US 2021/0196250 A1    Jul. 1, 2021

Related U.S. Application Data

(60) Provisional application No. 62/955,559, filed on Dec. 31, 2019.

(51) Int. Cl.
 *A61B 10/02* (2006.01)
(52) U.S. Cl.
 CPC .................. *A61B 10/0275* (2013.01)
(58) Field of Classification Search
 CPC ............ A61B 10/0275; A61B 10/0241; A61B 2010/0208
 See application file for complete search history.

(56) References Cited

U.S. PATENT DOCUMENTS

| | | | |
|---|---|---|---|
| 9,078,640 B1 | 7/2015 | An | |
| 2002/0082519 A1 | 6/2002 | Miller | |
| 2006/0116603 A1* | 6/2006 | Shibazaki | A61B 10/0096 600/562 |
| 2012/0022397 A1* | 1/2012 | Jarial | A61B 10/0275 600/567 |
| 2013/0030323 A1* | 1/2013 | Smith | A61B 10/0275 600/567 |
| 2013/0046201 A1 | 2/2013 | Cleon | |
| 2013/0102925 A1* | 4/2013 | McGhie | A61B 10/0233 600/567 |
| 2014/0277040 A1* | 9/2014 | Hayes | A61B 17/32002 606/170 |
| 2017/0231606 A1 | 8/2017 | White | |
| 2018/0333146 A1* | 11/2018 | Hallisey | A61B 8/0841 |

FOREIGN PATENT DOCUMENTS

WO    2014058667    4/2014

OTHER PUBLICATIONS

Extended European Search Report of EP21205328, completed Apr. 27, 2022.

* cited by examiner

*Primary Examiner* — Rene T Towa
(74) *Attorney, Agent, or Firm* — Wissing Miller LLP

(57) ABSTRACT

A core collector is shaped as a crescent in cross-section and has lateral sides formed into axially extending rows of axially spaced teeth. The arc angle of the crescent shape is sufficient to keep the core collector radially centered in a cannula by having the crescent's lateral sides bear against the inside of the cannula. The set of a core collector and cannula can be used in a known biopsy system to replace the known cannula and core collector of can be used in a new core biopsy instrument.

23 Claims, 42 Drawing Sheets

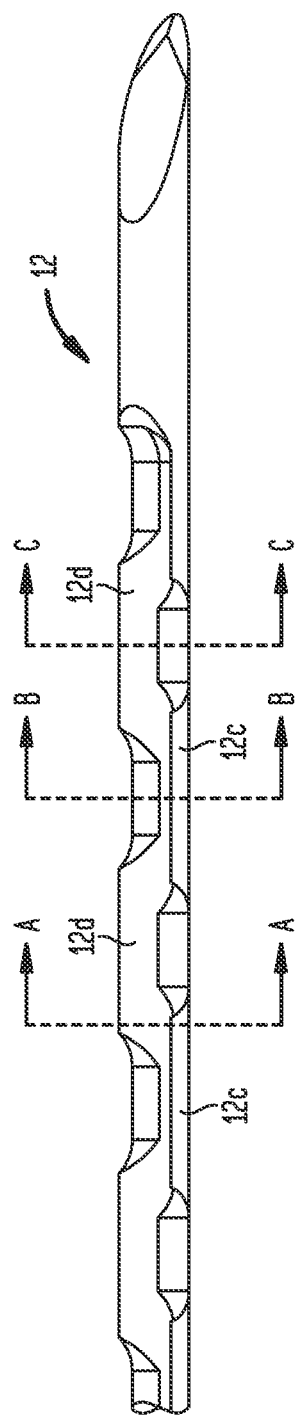

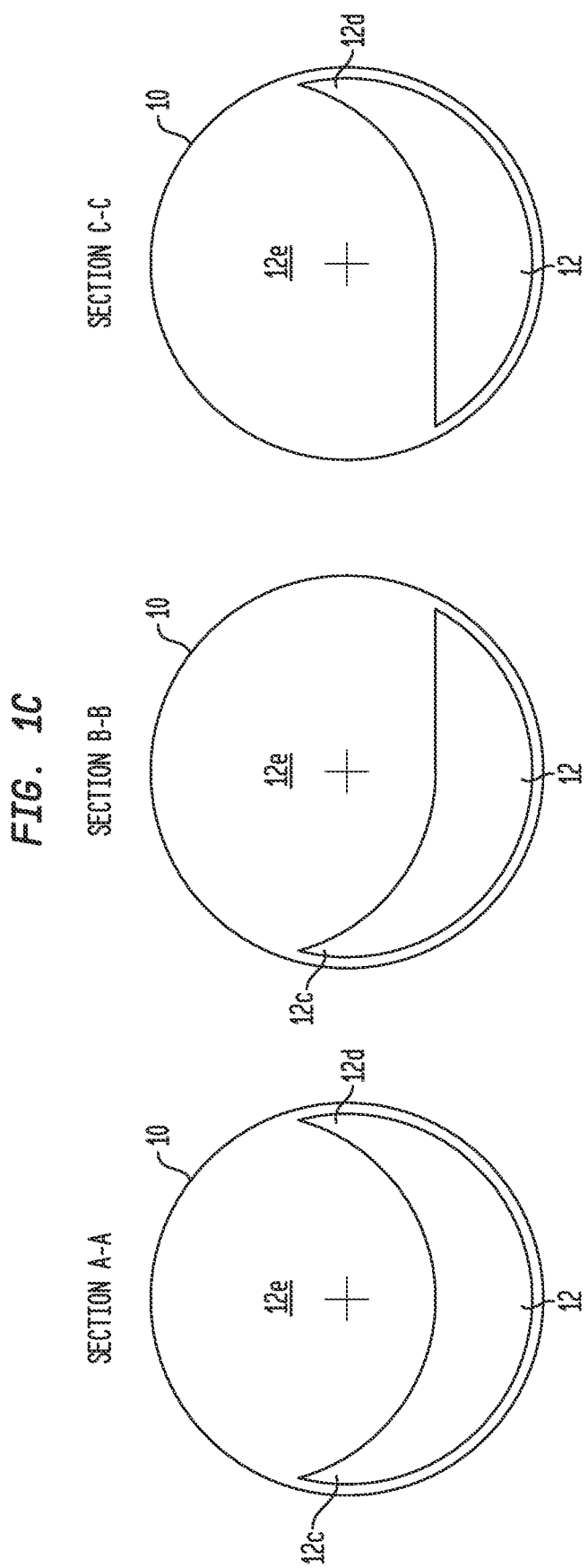

FIG. 1D1
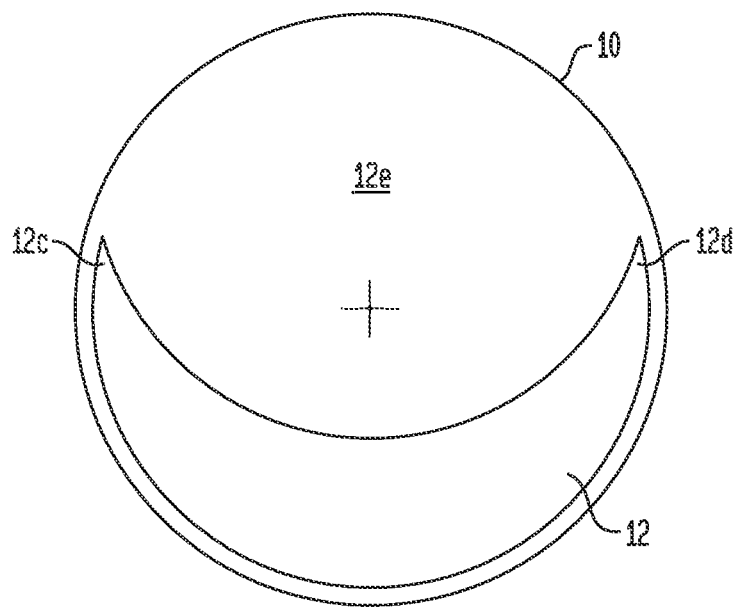
FIG. 1D2
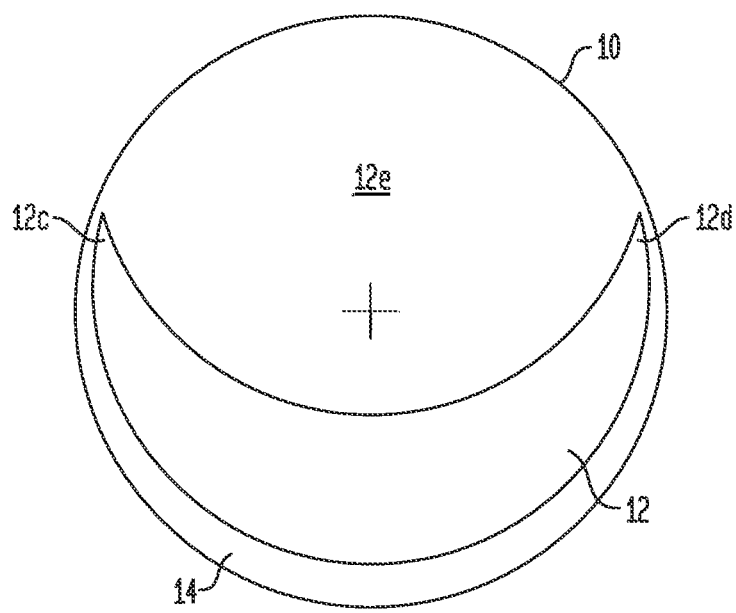

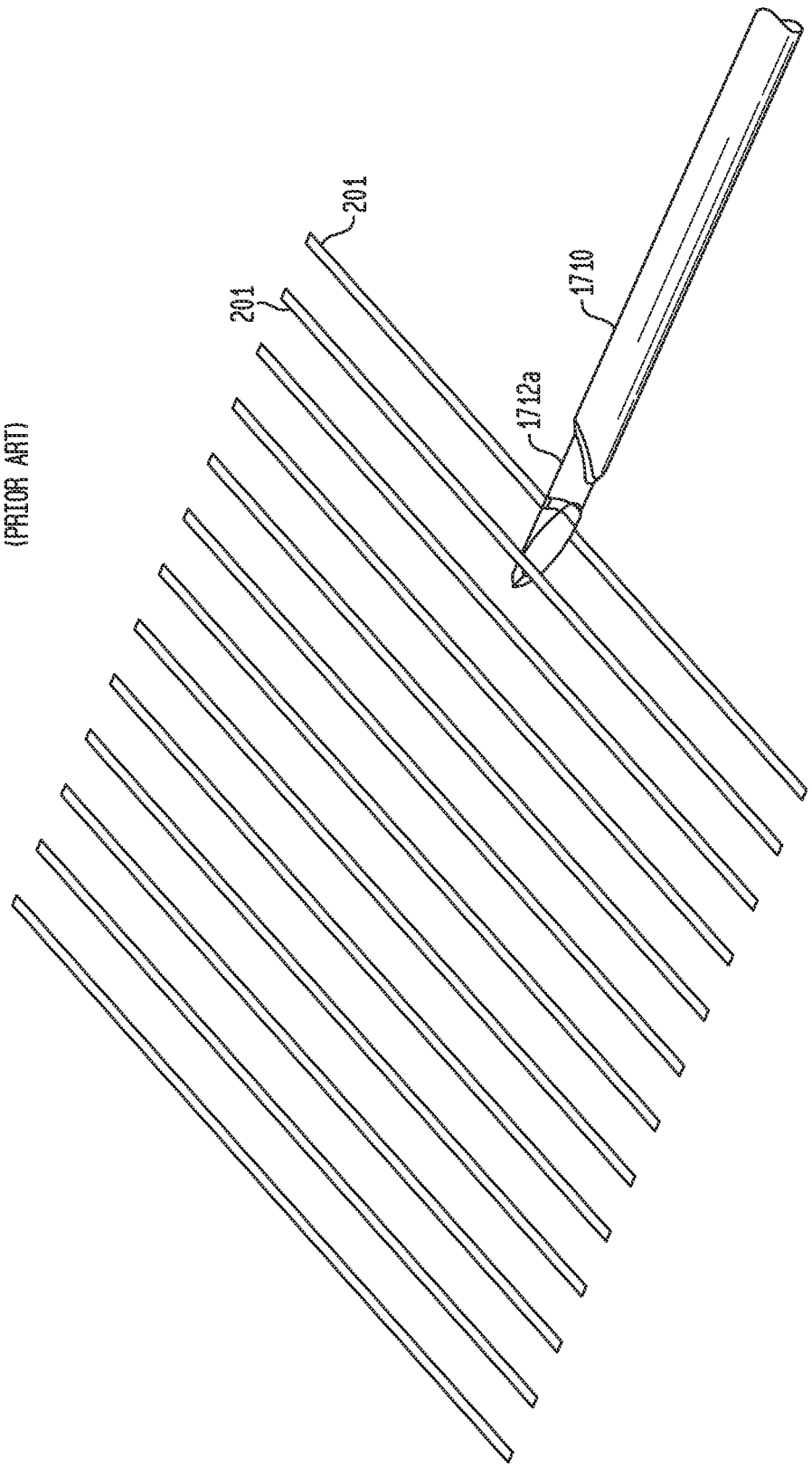

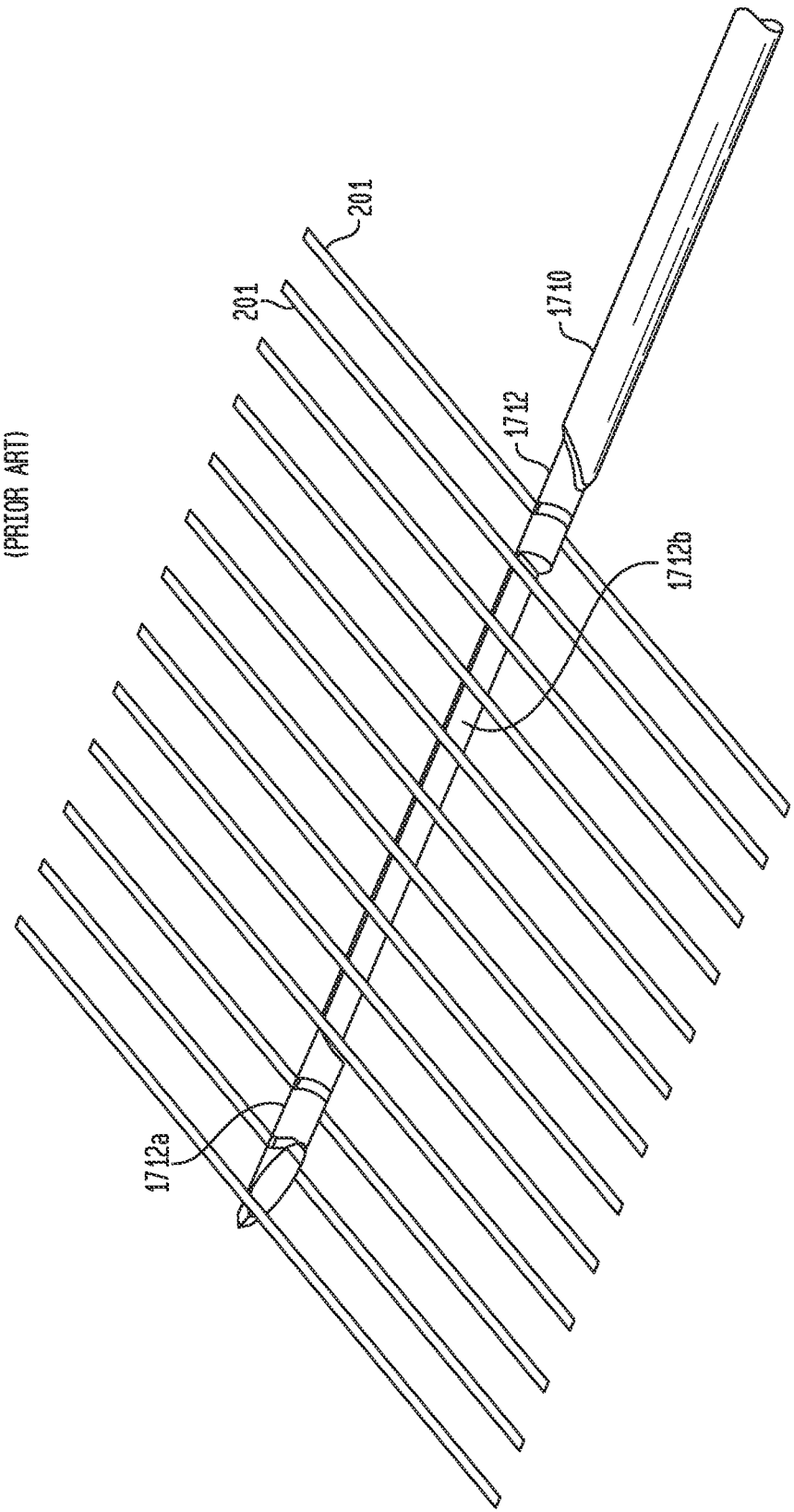

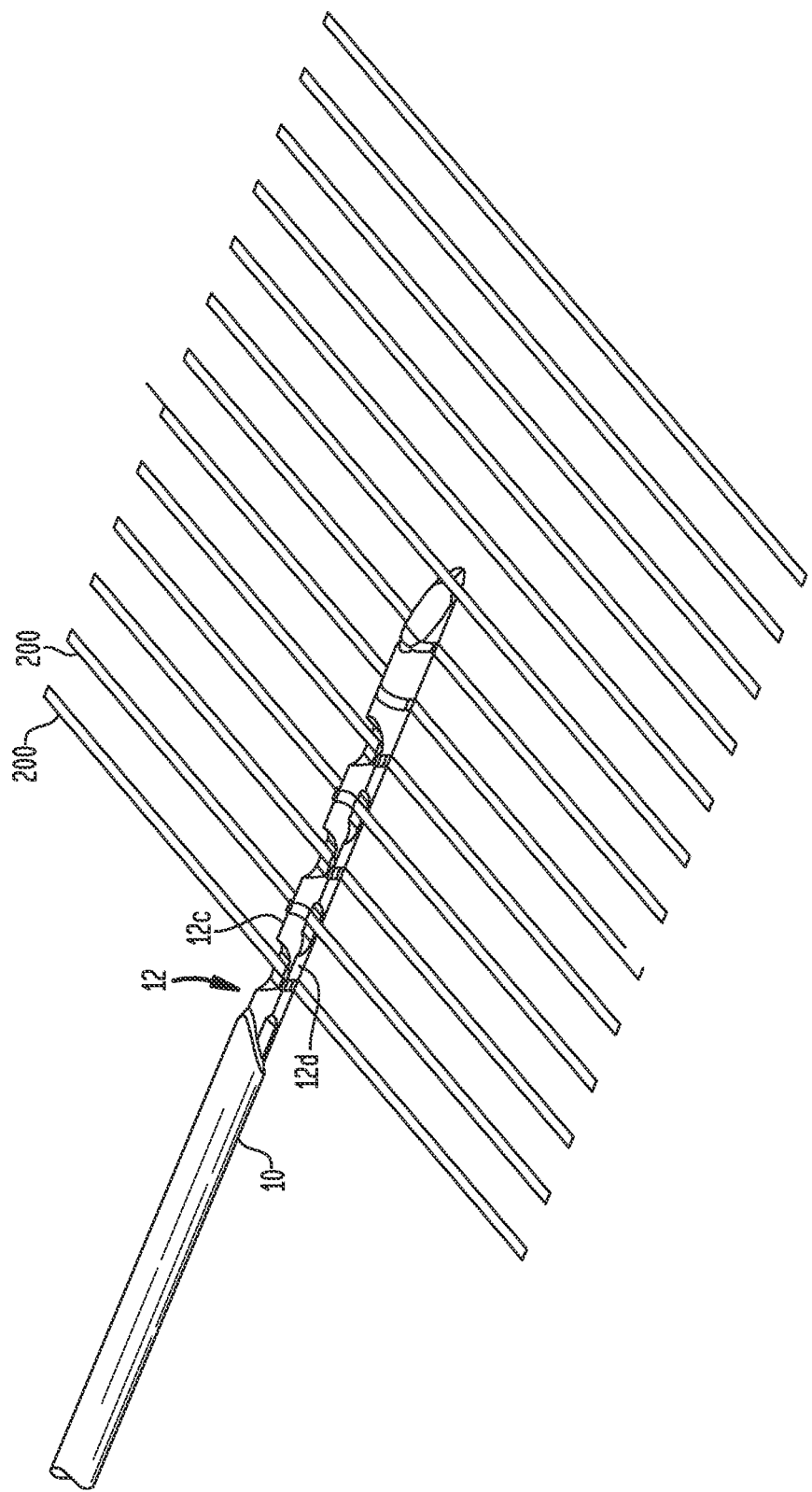

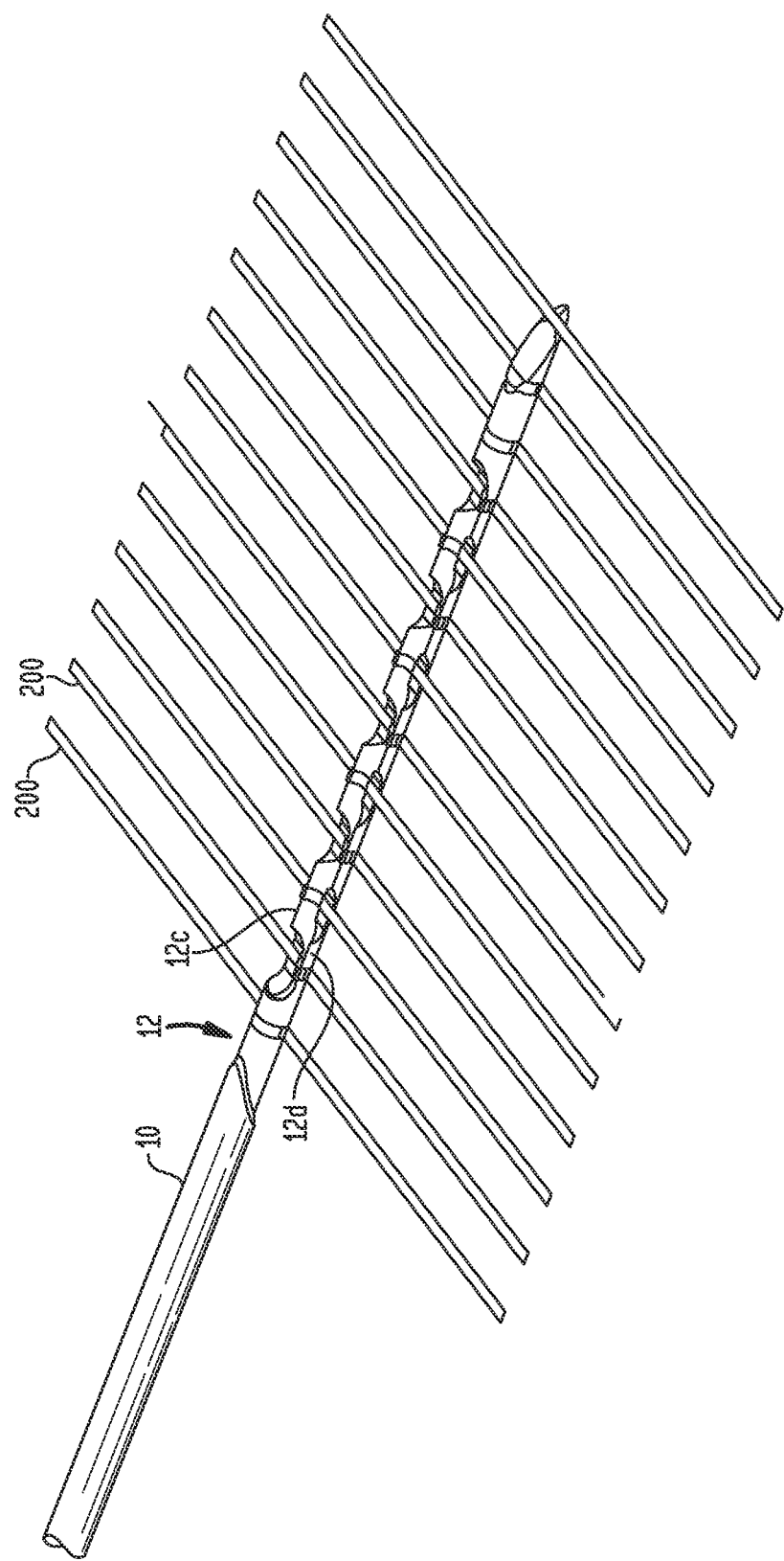

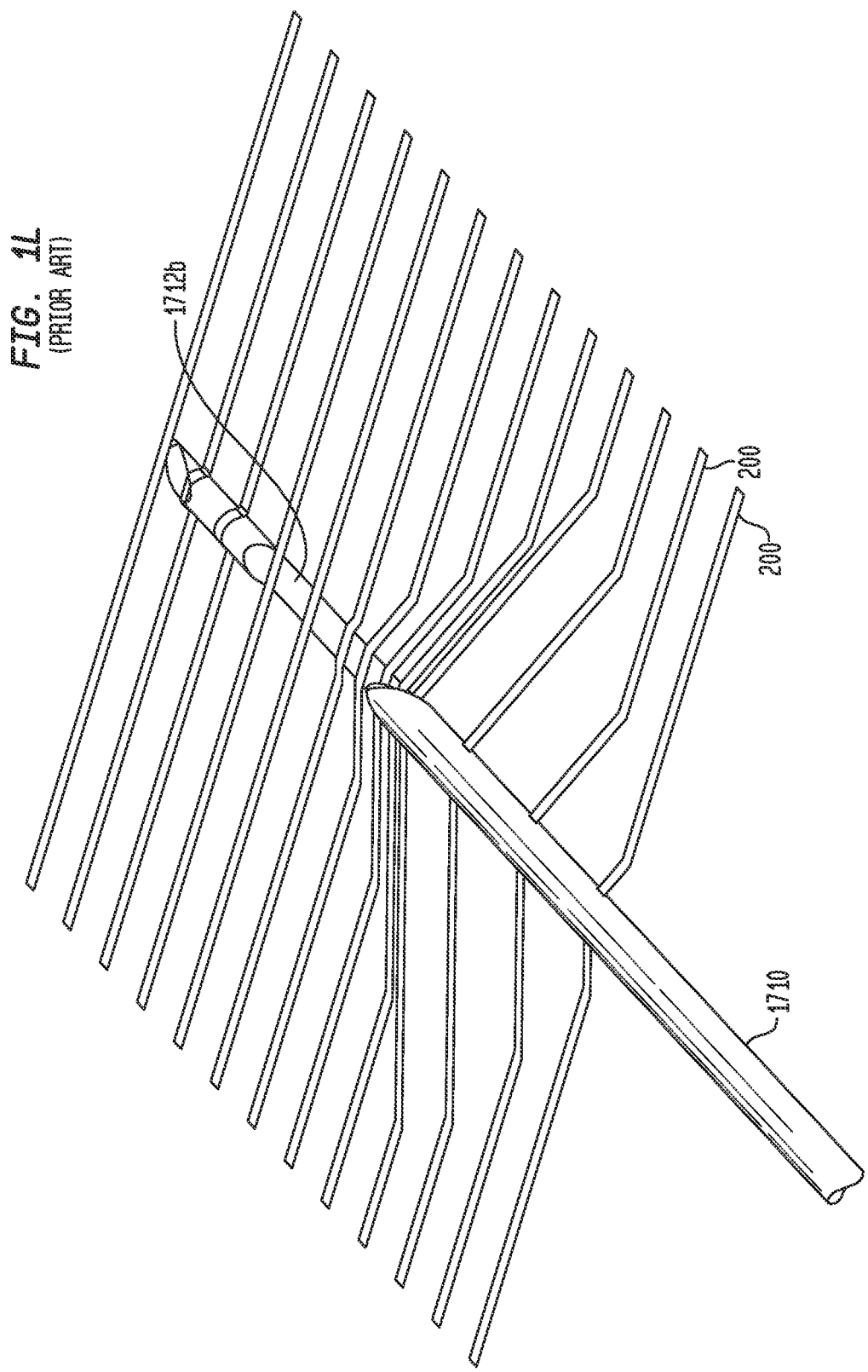

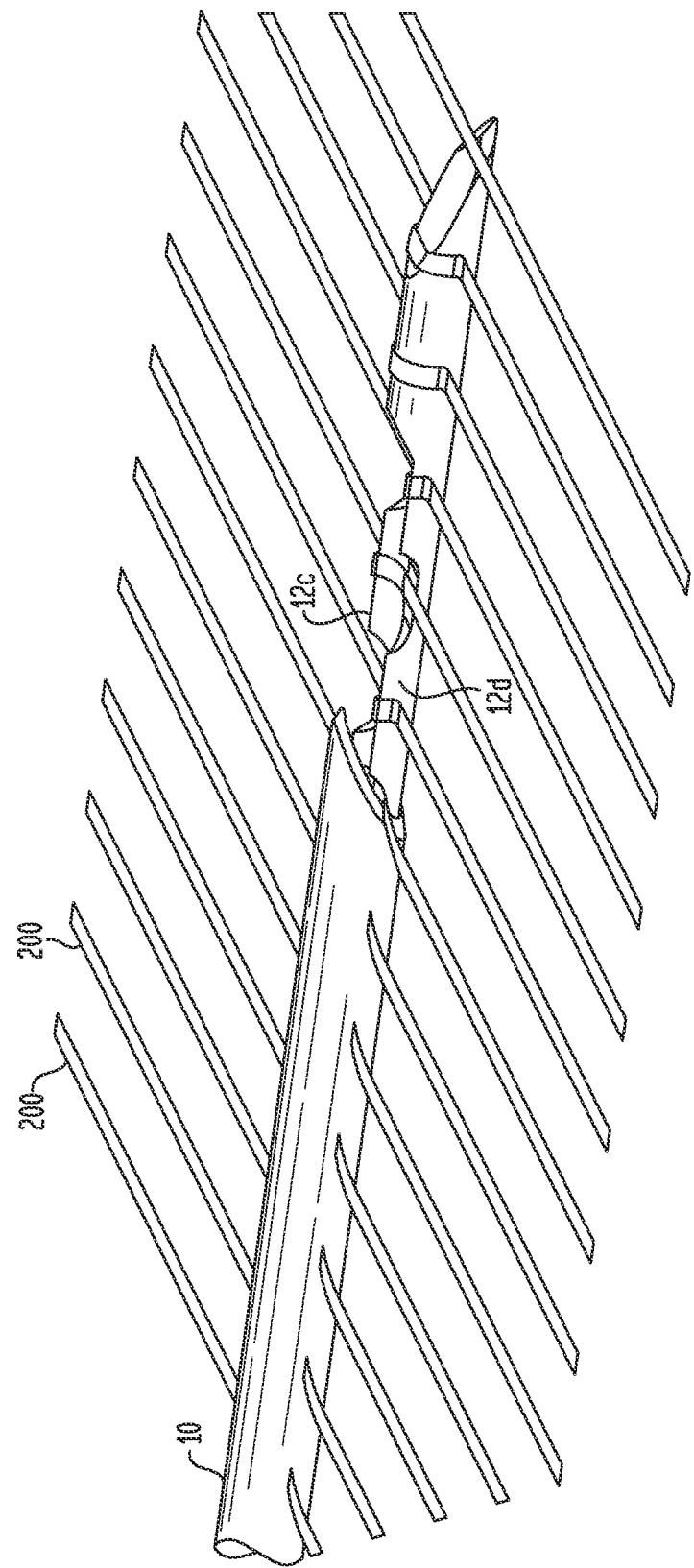

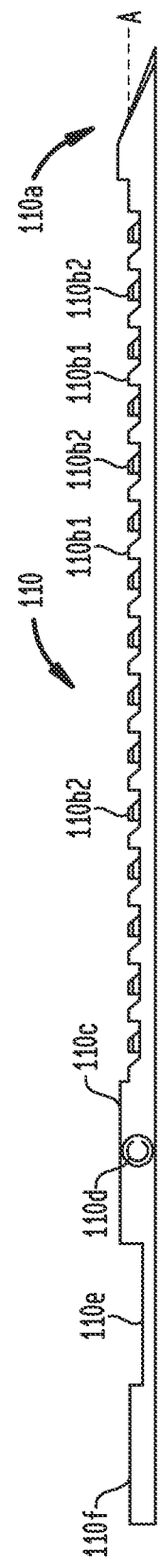

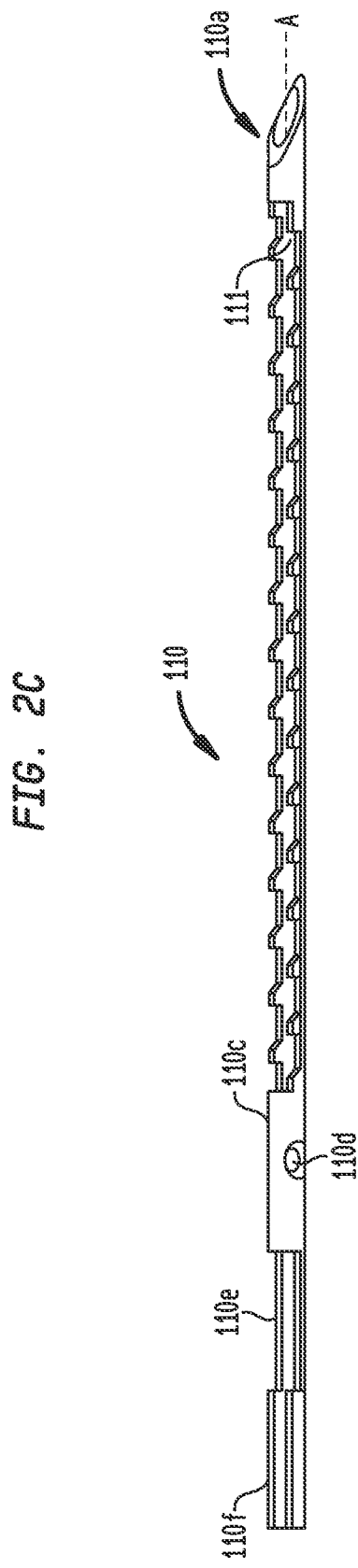

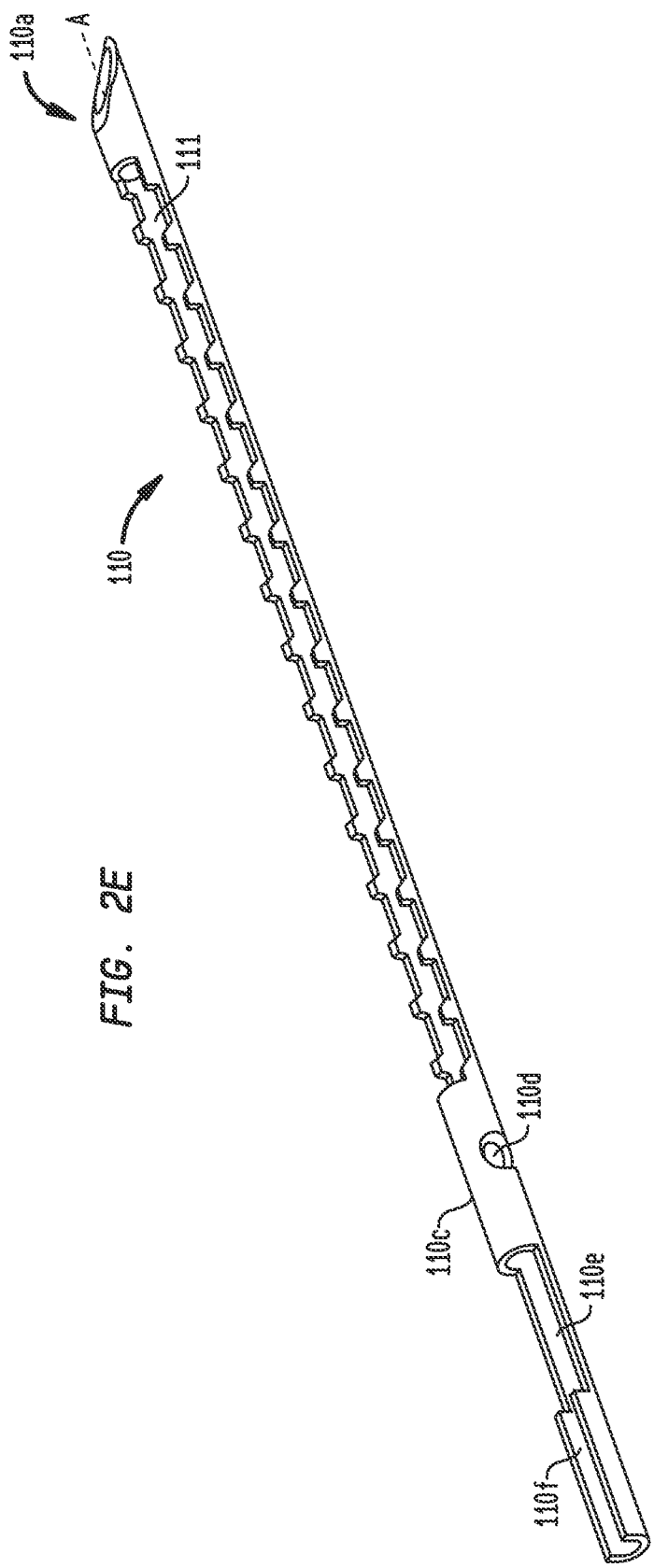

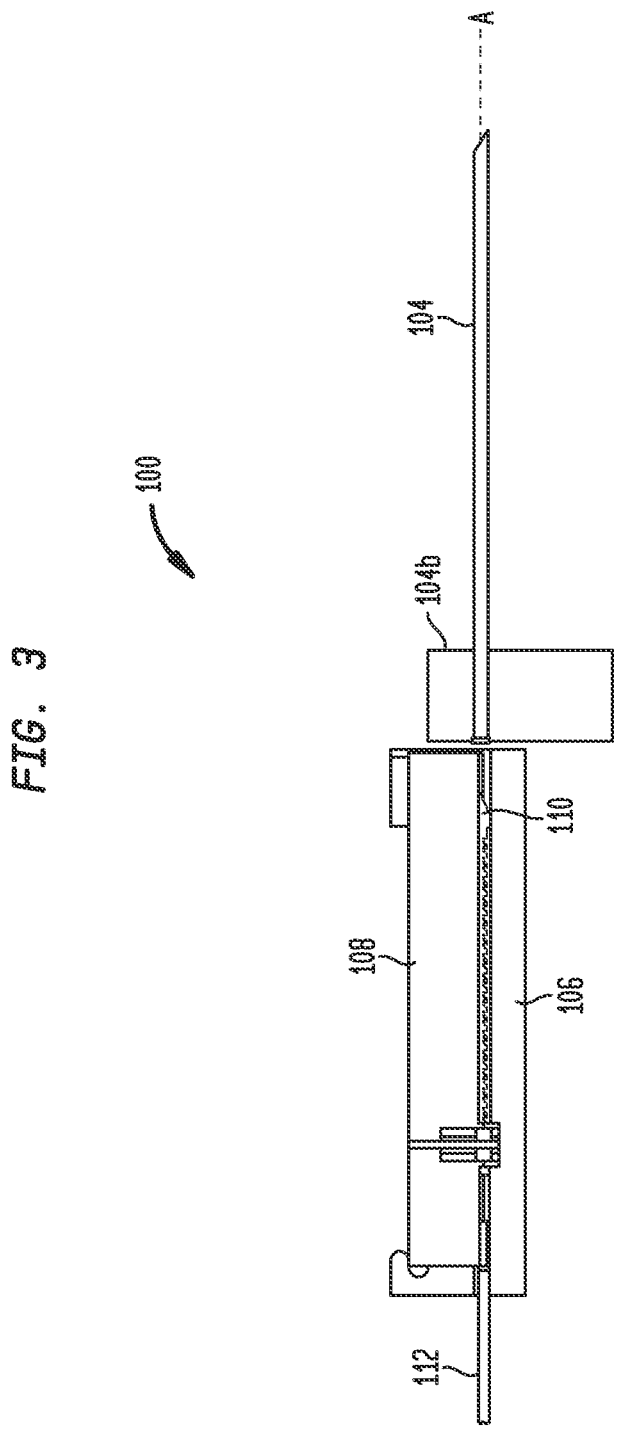

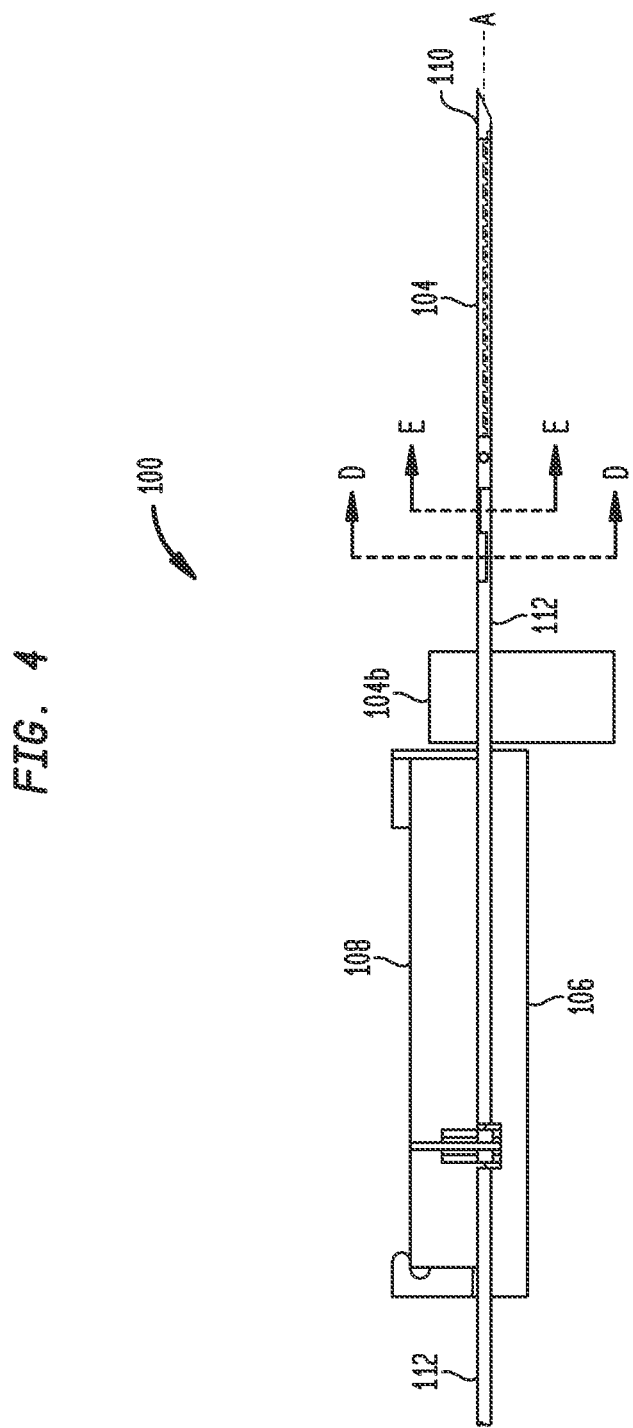

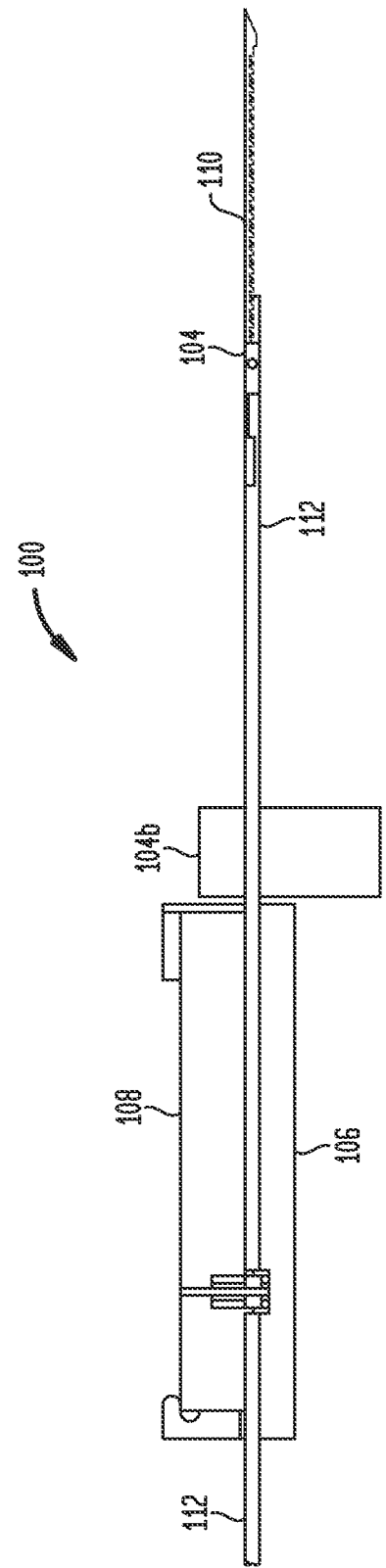

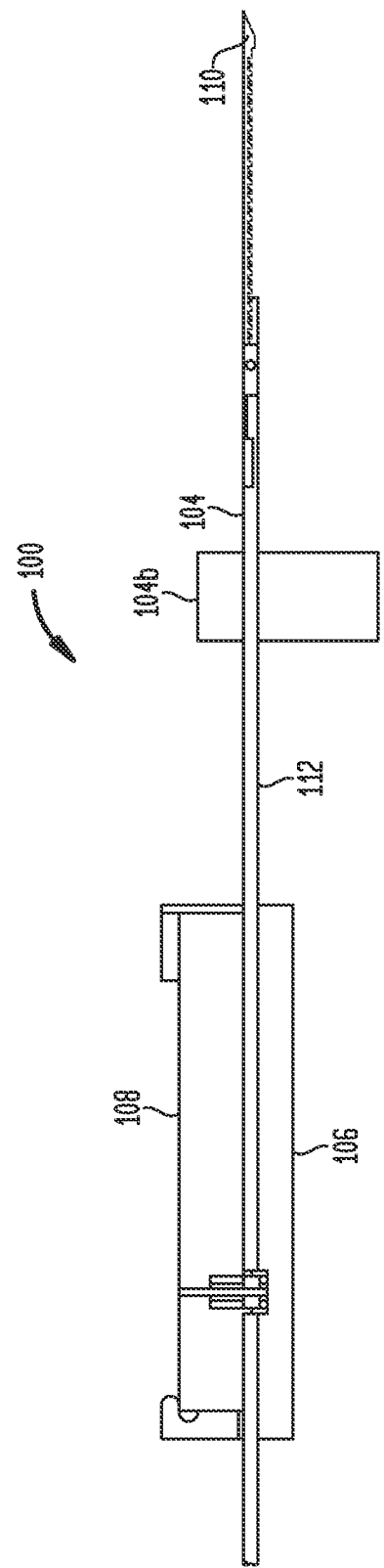

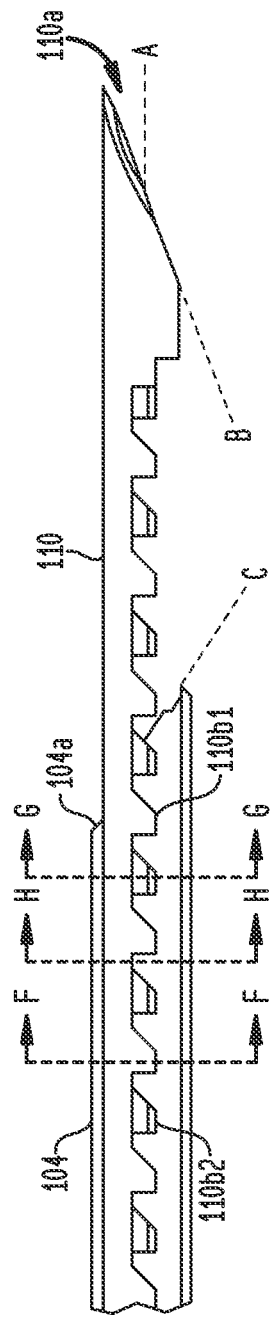

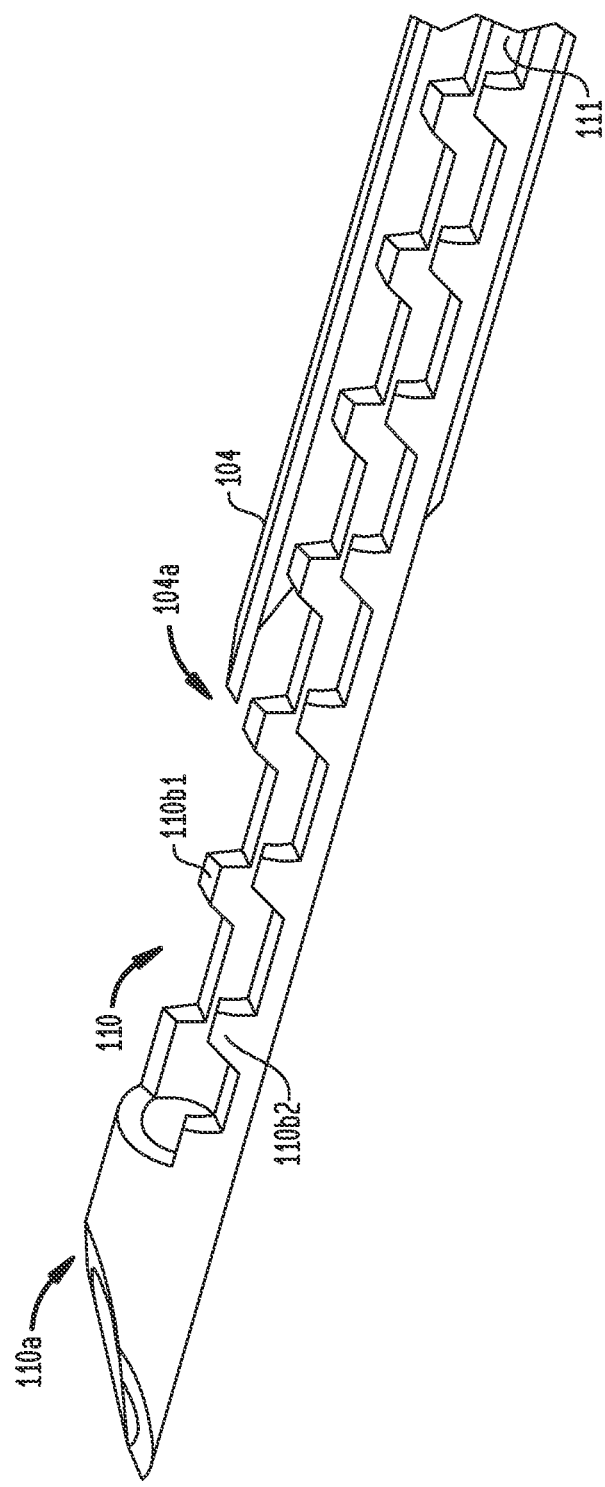

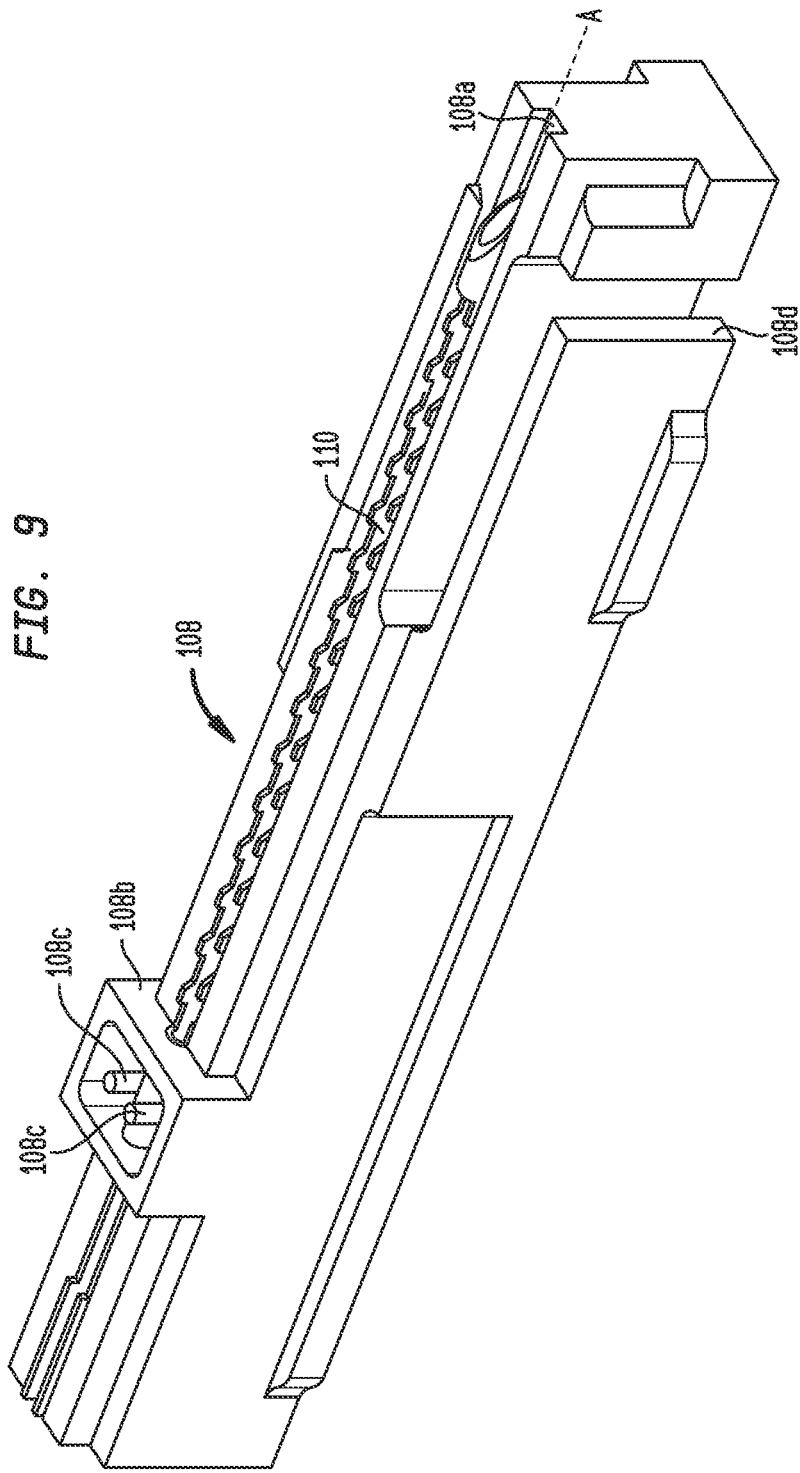

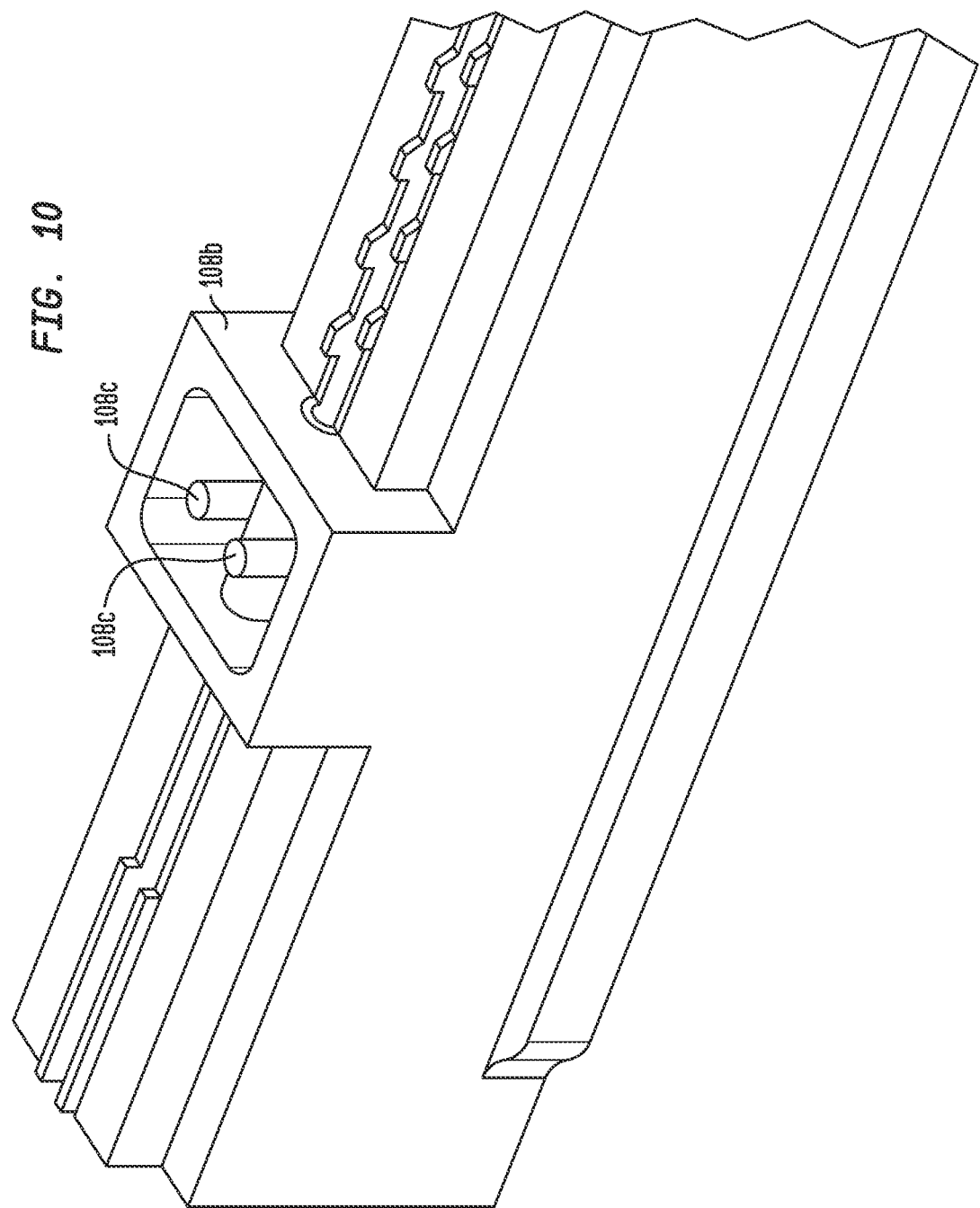

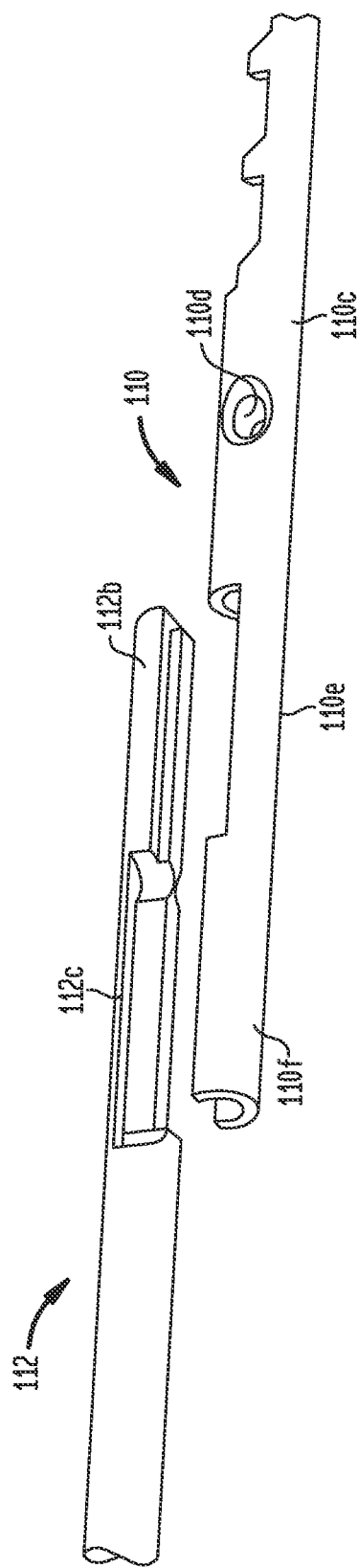

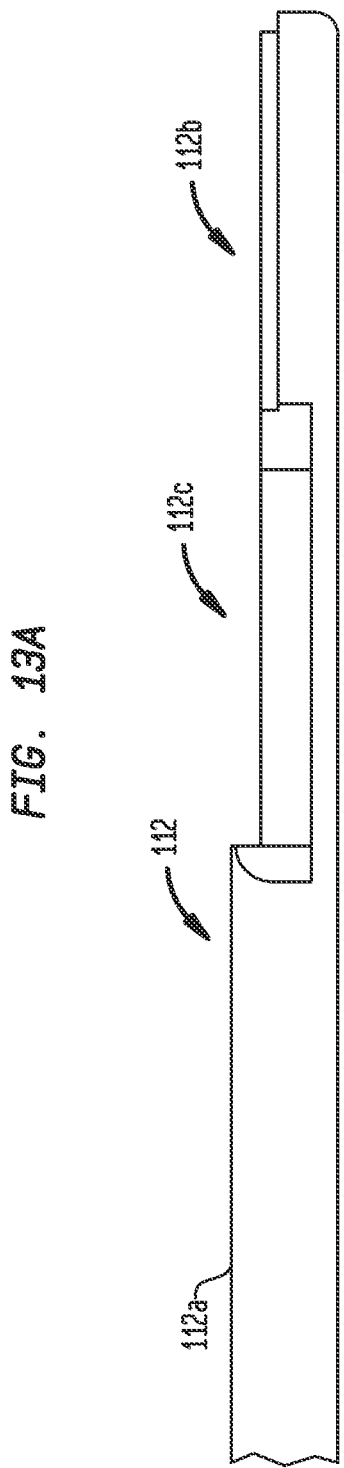

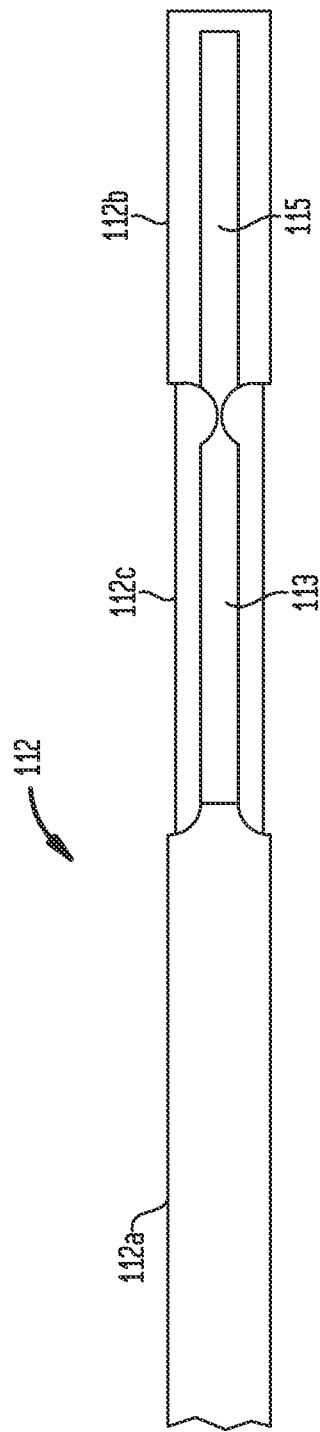

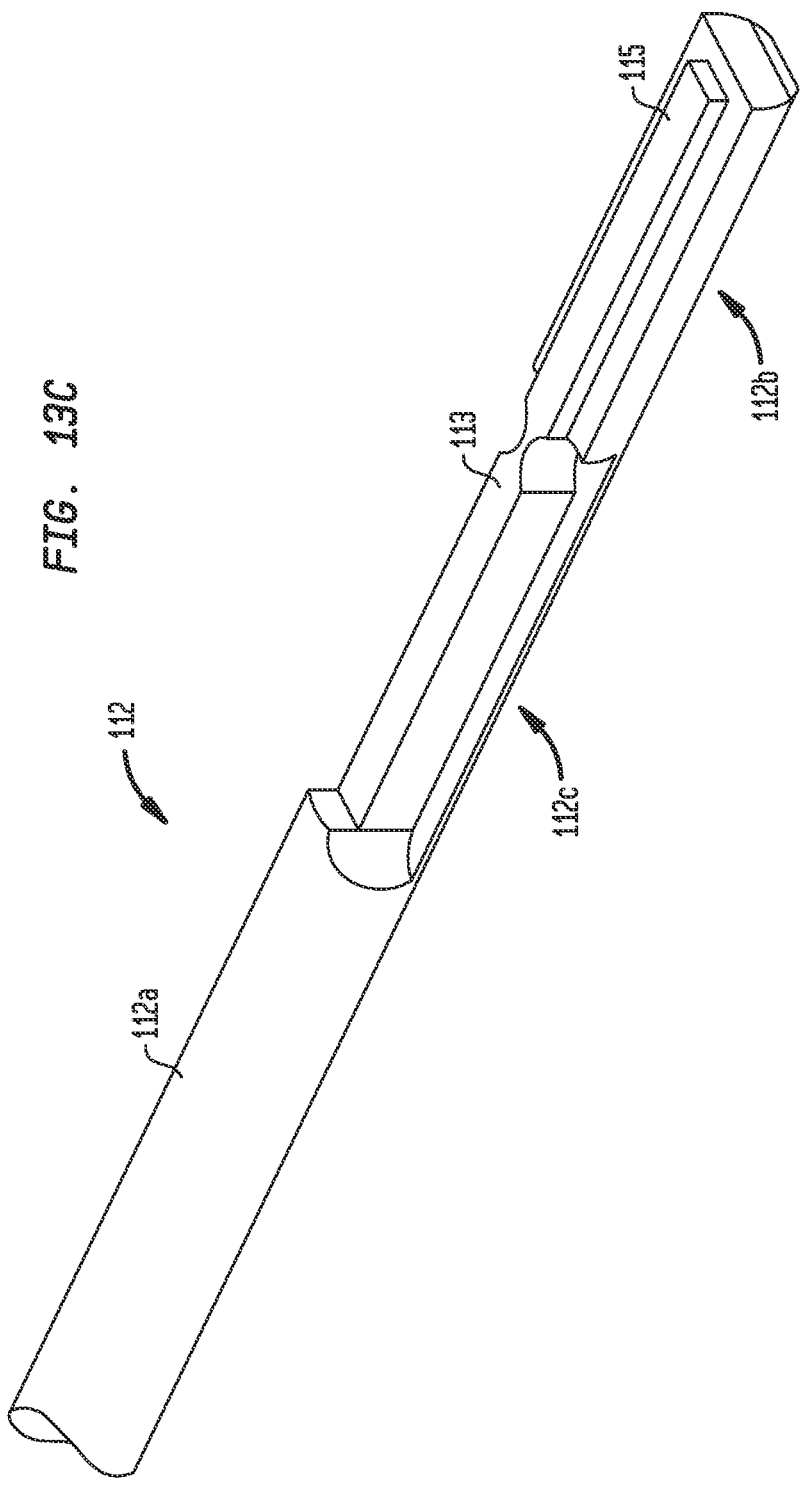

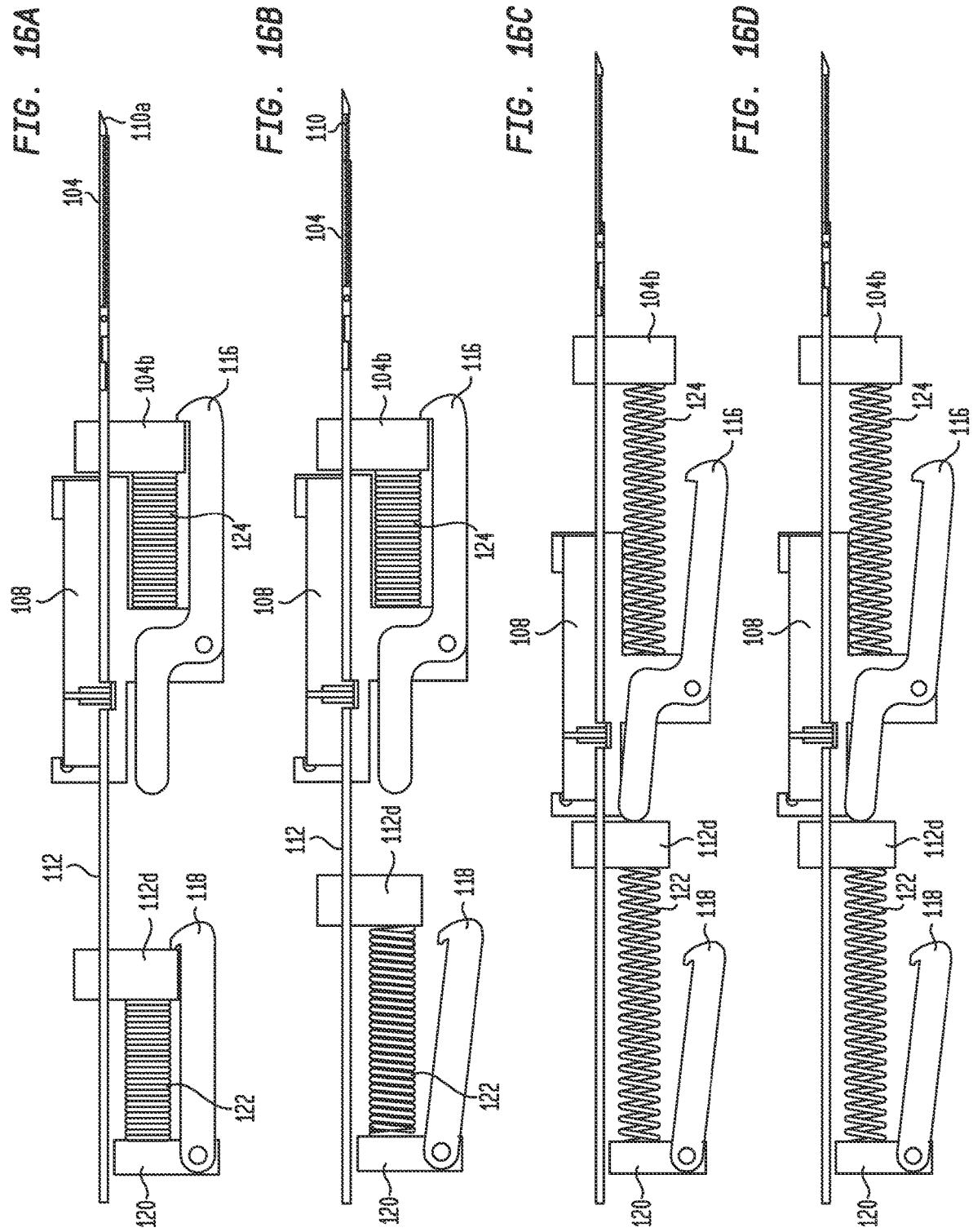

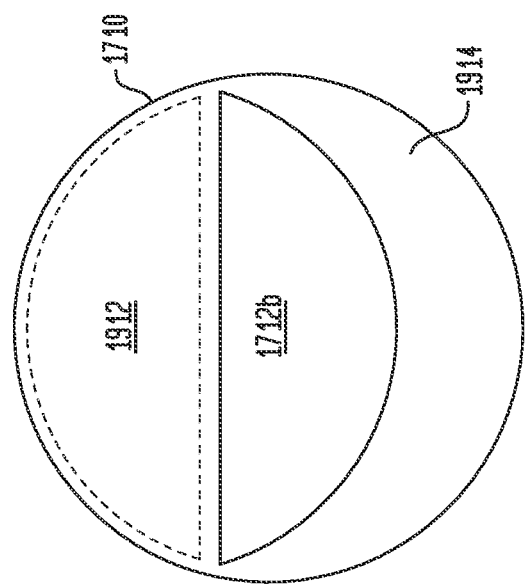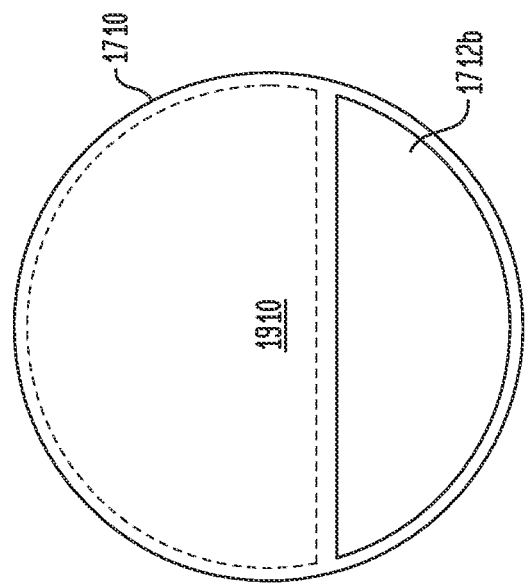
FIG. 19
(PRIOR ART)

BIOPSY SYSTEM WITH A CORE COLLECTOR THAT REMAINS RADIALLY CENTERED IN AN OUTER CANNULA WHILE SEVERING A TISSUE SAMPLE

REFERENCE TO RELATED APPLICATION

This application claims priority to provisional patent application Ser. No. 62/955,559 filed Feb. 4, 2020 and incorporates by reference the contents of said provisional application.

FIELD

This patent specification relates to medical devices for taking soft tissue samples including samples of prostate tissue. Some embodiments relate to a core collector that remains radially centered relative to an outer cannula that cuts a tissue sample and others include a device for driving a core collector and an outer cannula to sample tissue and to alternative core collector configurations.

BACKGROUND

When suspicious tissue is discovered in a patient's prostate or in another region through manual examination or an imaging modality such as ultrasound, MRI, X-ray imaging or the like, it may be desirable to perform a biopsy procedure to remove one or more samples of that tissue to help determine if the tissue contains cancerous cells, other cells of interest, or to gain other information. A biopsy may be performed using an open or a percutaneous method. For prostate tissue, typically a core needle device is used that enters the prostate transrectally (TRUS) or transperineally (TPUS). There are complex prostate sampling devices that require two or more people for the procedure. And, there are simpler devices some of which can be disposed after use on one patient. U.S. Pat. Nos. 5,546,957, 5,526,822, and 10,463,350, and published U.S. Patent application US 2016/0166331 A1 discuss examples of biopsy devices. The contents of said patents and published application are hereby incorporated by reference in this patent specification. A core biopsy device called Bard Magnum is believed to be commercially available from BD Bard in Tempe, Ariz. and there are comparable devices available from other manufacturers.

Typically, known prior art core biopsy instruments use a set of an outer cannula enclosing a core collector. Initially, the core collector is inside the cannula such that only a sharp tip of the core collector protrudes distally. In this configuration, the cannula and core collector as a unit are inserted in tissue until the sharp tip is at or inside a region of interest. Then, the core collection shoots distally in the tissue, and tissue springs into a notch that is just proximal from the sharp tip. A fraction of a second later, the cannula shoots distally to its initial position relative to the core collector. The cannula has a sharp distal end that in this distal motion cuts off some of the tissue that has entered the notch. The cannula and core collector can be withdrawn from the tissue and the sample taken out after moving the cannula and core collector axially relative to each other to expose the notch.

FIG. 17a illustrates a distal portion of a typical commercially available set of a cannula 1710 with a sharp distal end 1710a and a core collector 1712 with a sharp distal tip 1712a and a notch 1712b. FIG. 17b illustrates in less detail a complete commercially available set in which an engagement element 1712c is secured to the proximal end of core collector 1712. This element or similar engagement elements mate with respective driving mechanisms, such as spring-loaded mechanisms, for shooting distally first the core collector and then the cannula. FIG. 18 illustrates several relative positions of cannula 1710 and core collector 1712 in the vicinity of tissue 1810 to be sampled. The top illustration shows an initial position in which only the sharp distal end 1712a of core collector 1712 protrudes from cannula 1710 and notch 1712b is inside cannula 1710. Tissue 1810 in this example includes denser tissue such as a membrane 1810a and calcifications 1810b. The next illustration shows an intermediate point in the distal motion of core collector 1712. Notably, here the denser tissue deflects core collector upward, bending notch 1712b such that it fails to penetrate the denser tissue. The next illustration shows core collector 1712 fully extended distally from cannula 1710. In this relative position of cannula 171 and core collector 1712, some tissue (not shown) has entered notch 1712b from above. The next illustration shows outer cannula 1710 having advanced distally partway over notch 1712b of core collector 1712, cutting off some of the tissue in notch 1712b. The last illustration shows the final position of cannula 1710 relative to core collector 1712, in which the distal motion of cannula 1710 has cut off tissue in notch 1712b. However, because as illustrated there was a gap between the bottom surface of cannula 1710 and notch 1712b, two undesirable effects have occurred. One is that the reduced space between the upper side of notch 1712b and cannula 1710 during much of the distal motion of cannula 1710 over notch 1712b can elongate the tissue sample and/or can bunch it up or fragment it, thereby reducing its value as a representative sample of the original tissue. Another is that the volume of tissue that is collected can be substantially less that the initial volume of the space between the upper surface of notch 1712b and the inside of cannula 1710 seen in the top illustration. FIG. 19 illustrates this reduction in sample volume—the left side shows a potential volume 1910 for tissue between the upper surface of notch 1712b and the inside of cannula 1710, and the right side illustrates a reduced volume 1912 due to upward deflection of core collector 1712 at notch 1712b and a gap between the underside of notch 1712b and the lower part of cannula 1710 as discussed above.

This patent specification is directed to biopsy instruments that overcome several shortcomings of the known biopsy instruments as well as to provide other benefits, as discussed in detail below.

SUMMARY OF THE DISCLOSURE

A biopsy instrument according to some embodiments comprises: a tubular cannula that extends along a longitudinal axis and has an inside wall and a sharp distal end; a core collector that that fits in the cannula for motion relative thereto along said axis and has a sharp distal tip and a cradle portion extending proximally from the sharp tip along said axis; wherein (a) said cradle portion of the core collector has a convex bottom surface and a concave upper surface with side walls forming said cradle portion; (b) said side walls are configured to bear against the inside wall of the cannula when in the cannula to thereby keep the core collector centered in the cannula and to keep the bottom surface of the core collector against the inside wall of the cannula; (c) said side walls of the core collector comprise rows of teeth, with the teeth of each of said rows spaced from each along said axis; and (d) said teeth are configured to engage tissue that has entered said cradle while the core collector is protruding distally from the cannula and, as the cannula moves distally over the cradle, to keep said tissue from distorting as the cannula severs a tissue sample from surrounding tissue, thereby maintaining structural integrity of the tissue sample along said axis.

According to some embodiments, the biopsy instrument further comprises one or more of the following features: (1) said teeth are configured to engage said tissue to keep the tissue sample from compressing and/or stretching along said axis as the sample is being severed from surrounding tissue by the cannula moving over the cradle along said axis; (2) the teeth of each of said side walls are staggered relative to those of the other side wall such that some cross-sections contain teeth of both rows, some contain only a tooth of one of the rows, and some contain only a tooth of the other of said rows; and (3) in each of the cross-sections, a vertical distance between a top of the inside surface of the cannula and a tooth is no more than half the diameter of the inside wall; thereby providing a cutting action as the cannula moves over the cradle that facilitates maintaining structural integrity of the sample compared to integrity before being severed from surrounding tissue.

According to some embodiments, a biopsy instrument comprises: a tubular cannula that extends along a longitudinal axis and has an inside wall and a sharpened distal end; a core collector that that fits in said cannula for motion relative thereto along said axis and has a sharp distal tip and a cradle portion extending along said axis proximally from the sharp tip; wherein (a) said cradle portion of the core collector is elongated along said axis and has a convex bottom and a concave upper surface with side walls forming said cradle portion; (b) said side walls of the core collector extend above a mid-plane of said inside wall that coincides with said axis and comprise rows of teeth, with the teeth of each of said rows spaced from each along said axis and staggered such that some cross-sections of the cradle contain teeth of both rows, some contain only a tooth of one of the rows, and some contain only a tooth of the other of said rows; and (c) said teeth are configured to engage tissue that has entered said cradle while the core collector is protruding distally from the cannula and keep said tissue from distorting as the canula moves over the cradle to sever a tissue sample from surrounding tissue, thereby maintaining structural integrity of said tissue sample.

According to some embodiments, the instrument of the immediately preceding paragraph further comprises one or more of the following features: (1) said teeth are configured to maintain structural integrity of the tissue sample along said axis; (2) said teeth are configured to maintain structural integrity of the tissue sample in a direction across said axis; and (3) said teeth are configured to maintain structural integrity of the tissue sample both along said axis and in a direction across said axis.

According to some embodiments, a biopsy instrument comprises: an axially extending tubular cannula that has an inside wall and a sharp distal end; an axially extending core collector that has a sharp distal tip and a proximal portion extending proximally from the sharp tip and configured to fit in the cannula for relative motion between the cannula and the core collector; wherein said proximal portion of the core collector is, in some but not all cross-sections thereof, crescent-shape with a concave upper surface and a convex bottom and lateral tips, said crescent shape extending over a sufficiently large arc angle to keep said proximal portion radially centered in said cannula and said bottom against the inside wall of the cannula by said lateral tips bearing against said inside wall, thereby providing an open space for a tissue sample; and wherein each of said lateral tips of the crescent-shaped proximal portion of the core collector comprises a row of teeth axially spaced from each other.

According to some embodiments, the instrument of the immediately preceding paragraph further comprises one or more of the following features: (1) said bottom of the proximal portion of the core collector extends over half the circumference of the cannula's inside wall; (2) said teeth are polished smooth; (3) said proximal portion of said core collector is machined from a solid rod; and (4) the instrument further includes a driving mechanism engaging proximal ends of the cannula and core collector to selectively drive distally first the core collector so that said proximal portion of the core collector protrudes distally from the cannula by a selected distance and then the cannula so that the sharpened distal end of the cannula advances to said sharp distal end of the core collector to cut a tissue sample extending in said open space.

According to some embodiments, a method comprises: providing an axially extending core collector that is crescent shaped in at least some cross-sections and comprises two rows of teeth formed at lateral sides of the crescent shape, with the teeth of each row axially spaced from each other; a cannula configured to surround the core collector for relative motions between the cannula and core collector, wherein the crescent shape extends over an arc angle sufficient to keep the core collector radially centered in the cannula by the lateral sides bearing against the inside of the cannula; introducing the cannula and core collector into tissue and driving a selected length of the core collector distally from the cannula and into tissue; thereafter, driving the cannula distally over said core collector to thereby sever a sample of said tissue while keeping the core collector radially centered in said cannula; and extracting a tissue sample collected in an open space between the cannula and the crescent-shaped core collector.

According to some embodiments, the method further includes one or more of the following steps: (1) driving the core collector with said tissue sample therein proximally to a position aligned with a cartridge that is releasably secured to a handle supporting the cannula and core collector and releasably latching the core collector to the cartridge; an removing the cartridge with the core collector latched thereto from said handle; and (2) extracting a structurally integral tissue sample from said core collector after removal thereof from said handle.

According to some embodiments, a biopsy instrument comprises: an axially extending core collector that is crescent shaped in at least some cross-sections, and has a convex underside and a concave upper surface; wherein said core collector comprises two axially extending rows of teeth formed at lateral sides of the crescent shape, with the teeth of each row axially spaced from each other; and a tubular cannula having an inside wall and a sharp distal end; wherein (a) the cannula is configured to receive the core collector for relative motion between a first relative position in which a selected length of the core collector extends distally from the cannula and a second position in which the cannula has moved distally over and relative to the core collector from said first position; and (b) the crescent shape of the core collector extends over an arc angle sufficient to keep the core collector radially centered in the cannula due to the lateral sides of the core collector bearing against the inside wall of the cannula to thereby keep the convex underside of the core collector from moving away from the cannula inside due to forces acting on the core collector in a direction transverse to the axial length of the core collector.

According to some embodiments, the instrument of the immediately preceding paragraph further comprises one or more of the following features: (1) said arc extends over an angle that is at least a half-circle but is less than a full circle; and (2) said arc extends over an angle that approaches a half-circle.

BRIEF DESCRIPTION OF THE DRAWINGS

FIG. 1b is a partial side view of a core collector, and

FIG. 1c shows cross-sections of a core collector, according to some embodiments.

FIG. 1d illustrates that a core collector according to some embodiments remains centered in a cannula compared with a known combination of a core collector and a cannula that does not.

FIGS. 1e through 1m illustrate important benefits of a core collector and cannula according to some embodiments compared with a known combination of a core collector and a cannula.

FIG. 2b is a side view of a core collector, and

FIGS. 2c-2e are perspective views of a core collector, according to some embodiments.

FIG. 3 is otherwise like FIG. 2a but shows a cartridge releasably secured in a handle according to some embodiments.

FIG. 4 is otherwise like FIG. 3 but shows a core collector advanced into a cannula according to some embodiments.

FIG. 5 is otherwise like FIG. 4 but shows a core collector advanced distally out of a cannula according to some embodiments.

FIG. 6 is otherwise like FIG. 5 but shows a cannula advanced distally over a core collector according to some embodiments.

FIG. 7 is an enlarged side view of a distal portion of a core collector and a sectional view of a cannula partly advanced over the core collector according to some embodiments.

FIG. 8 is a perspective view of the portions of a cannula and core collector seen in FIG. 7 according to some embodiments.

FIG. 9 is a perspective view of a cartridge according to some embodiments.

FIG. 10 is an enlarged perspective view of a cartridge according to some embodiments.

FIG. 12 is a perspective view of a drive rod interlocking with a proximal portion of a core collector according to some embodiments.

FIG. 13a is a side view,

FIG. 13b is a plan view, and

FIGS. 13c and 13d are perspective views of a distal portion of a drive rod according to some embodiments.

FIGS. 16a-16d schematically illustrate steps in the operation of a spring-loaded cannula and a spring-loaded core collector according to some embodiments

FIG. 19 shows cross-sections at the position of a notch of a typical known core collector in different relative axial position of a cannula and a core collector.

DETAILED DESCRIPTION

A detailed description of examples of preferred embodiments is provided below. While several embodiments are described, the new subject matter described in this patent specification is not limited to any one embodiment or combination of embodiments described herein, but instead encompasses numerous alternatives, modifications, and equivalents. In addition, while numerous specific details are set forth in the following description to provide a thorough understanding, some embodiments can be practiced without some or all these details. Moreover, for the purpose of clarity, certain technical material that is known in the related art has not been described in detail in order to avoid unnecessarily obscuring the new subject matter described herein. It should be clear that individual features of one or several of the specific embodiments described herein can be used in combination with features of other described embodiments or with other features. Further, like reference numbers and designations in the various drawings indicate like elements.

Figure 1A:
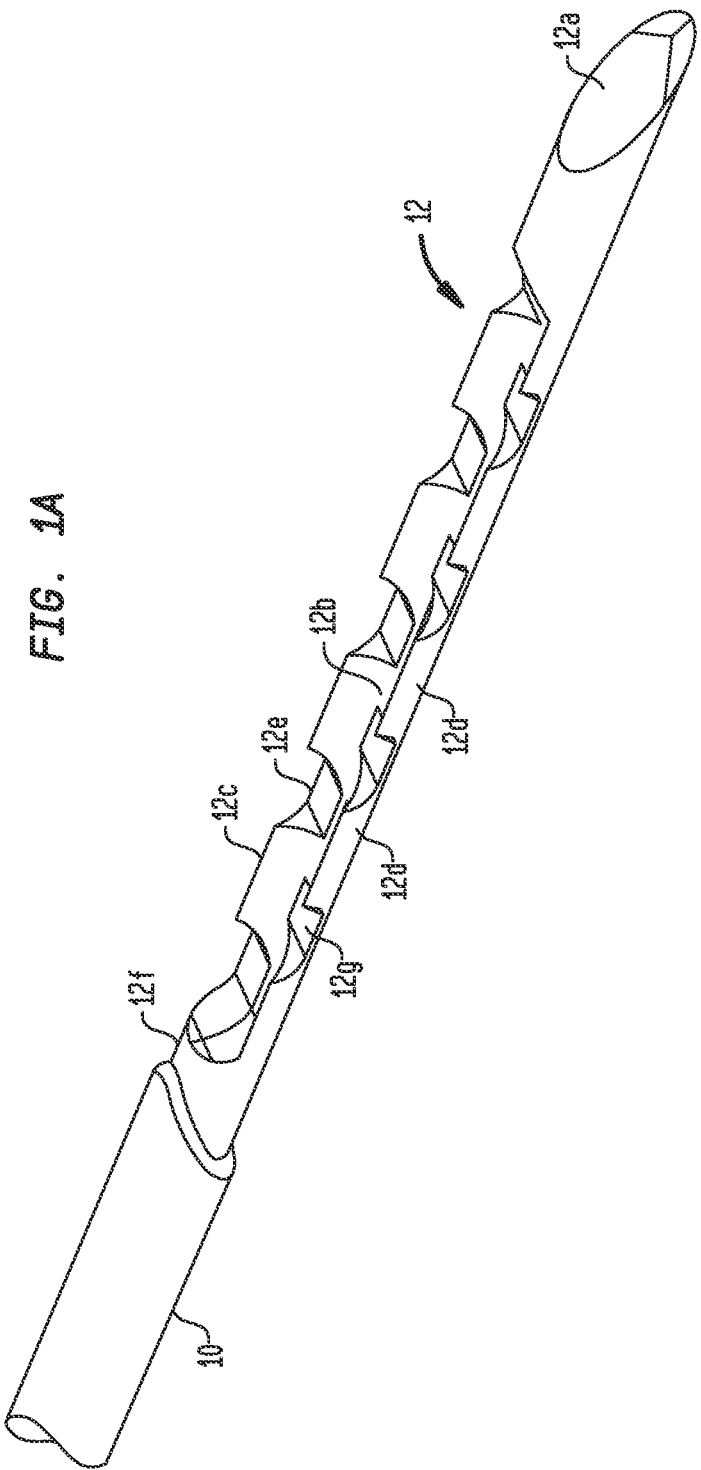
FIG. 1a is a partial perspective view of a cannula and a core collector.
Figure 17A:
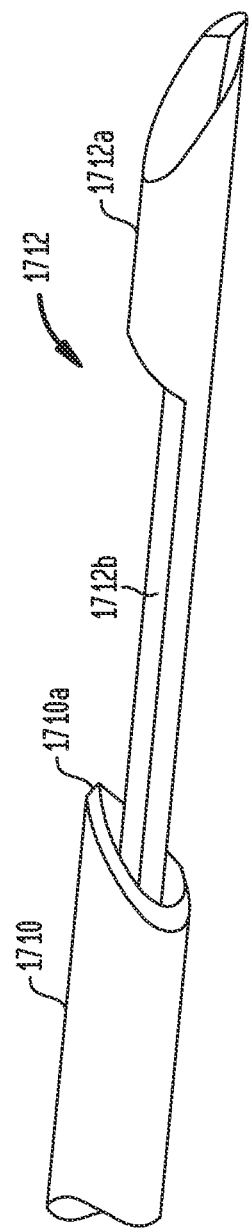
FIG. 17a is a perspective view of a distal portion of a typical known set of core collector with a side notch capture of tissue and an outer cannula.
Figure 17B:
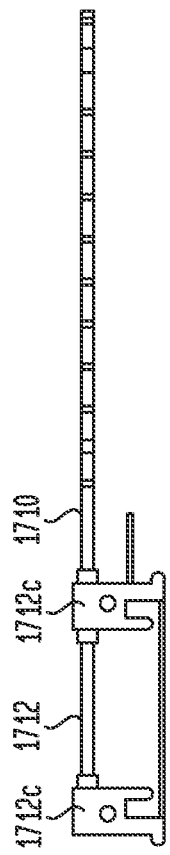
FIG. 17b shows the entirety of such a set.
Figure 18:
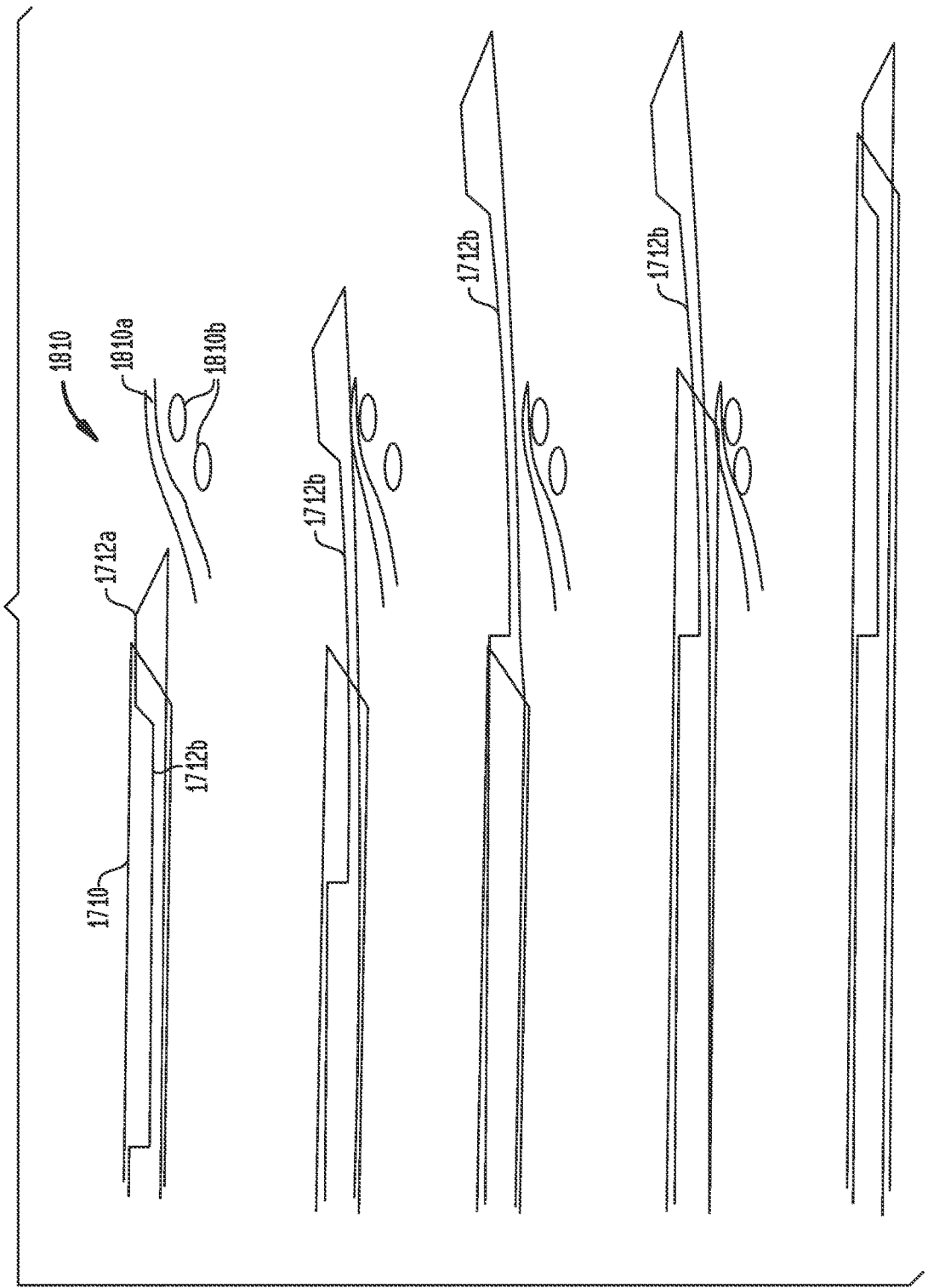
FIG. 18 shows a firing sequence of a typical known core biopsy instrument.

FIG. 1a illustrates, in a partial perspective view, distal portions of an outer cannula 10 and a core collector 12 according to some embodiments. They are very different from known core collectors of the type shown in FIGS. 17a-b. The proximal portions of cannula 10 and core collector 12 are not shown in this view but as known in the art they typically include attachments to engage driving devices for distally firing the core collector and cannula in succession into tissue, for example attachments in the form of engagement element 1712c shown in FIG. 17b. The core collector typically is longer than the cannula by at least the axial length of the core collector portion extending distally from the cannula as seen in FIG. 1a. Notably, core collector 12 has an axially extending, rounded-bottom trough 12b defined as the space between two parallel, axially extending rows of teeth 12c and 12d. Teeth 12c are axially spaced from each other by notches 12e. The distal tooth 12c is similarly spaced from tip 12a and the proximal tooth 12c is similarly spaced from a solid portion 12f of core collector 12. Teeth 12d are similarly spaced from each other axially by notches 12g and the distal and proximal teeth 12d are similarly spaced from tip 12a and solid portion 12f.

FIG. 1b illustrates core collector 12 and the positions of cross-sections A-A, B-B, and C-C, and FIG. 1c illustrates those cross sections. At left, FIG. 1c shows that section A-A intersects both a tooth 12c and a tooth 12d, and that at this section core collector 12 is crescent-shaped, with trough 12e at the concave side of the shape. Teeth 12c and 12d are formed by the lateral tips of the crescent shape. In this cross-section, the crescent-shape has a concave upper surface and a convex bottom and lateral tips, and this crescent shape extends over a sufficiently large arc angle to keep the core collector radially centered in the cannula, and to keep the bottom of the core collector against the inside wall of the cannula, by said lateral tips bearing against the inside wall of the cannula. The crescent shape preferably extends over an arc angle of roughly 180 degrees, but the angle can be somewhat more or less. This shape provides an open space above the concave side of the crescent to hold sample tissue and keeps the bottom of the core collector from rising and reducing the open space 12e.

At center of FIG. 1c, section B-B is through a tooth 12c and a notch or gap 12g between two adjacent teeth 12d, and at right in FIG. 1c section C-C is through a tooth 12d and a notch or gap 12e between two adjacent teeth 12c. Note that in the axial direction each tooth 12c overlaps a bit with a tooth 12d. Core collector 12 can be machined from a solid rod of a material such as 304 SS (stainless steel). The teeth or at least the tooth edges preferably are polished smooth to help with retaining a tissue sample as intact as possible and in readily releasing the tissue sample after removal of cannula 10 and core collector 12 from the patient.

FIG. 1d illustrates an important benefit of the configuration of core collector 12. At left, FIG. 1d shows the potential space 12e for a tissue sample between the upper surface of trough 12b and the inside of cannula 10. At right, FIG. 1d shows that this potential space for a tissue sample is nearly the same even when core collector 12 is deflected up as much as possible, and only a small gap 14 is possible between the bottom side of core collector 12 and the inside of cannula 10. This is so because teeth 12c and 12d cannot go any further up in cannula 10 as they bear against the diminishing size of the space in cannula 10 that is above the crescent shape. This is in marked contrast to the case of a known cannula and core collector unit as illustrated in FIG. 17. As a result, a tissue sample of greater cross-section can be extracted for the same diameter canula than with known instruments and the sample can have greater integrity and retain a shape closer to its original shape in surrounding tissue, and thus the sample can have enhanced clinical value compared with samples extracted with known cannula and core collectors of the type seen in FIG. 17. In tests comparing performance of a cannula 10 and core collector 12 with a commercially available cannula and core collector as illustrated in FIG. 17 (from a Bard Magnum Biopsy Gun), the samples when using core collector 12 were larger, more consistent, and retained better integrity.

Cannula 10 and core collector 12 can be used in place of the cannula and core collector in known biopsy instruments, for example instruments such as the Bard Magnum instrument identified above, with suitable attachments at the proximal ends of the cannula and core collector to mate with driving mechanisms in such known biopsy devices. Or, core collector 12 can be used in a known instrument in place of the known core collector while the known cannula remains in place. Or, cannula 10 and core collector 12 can be used in biopsy instruments as described below. If used in an instrument as described below, core collector 12 replaces core collector 110 described below.

As noted above, keeping the core collector centered in the cannula brings about important benefits compared to known biopsy devices. Some of these benefits are highlighted in FIGS. 1e through 1m discussed below.

Figure 1F:
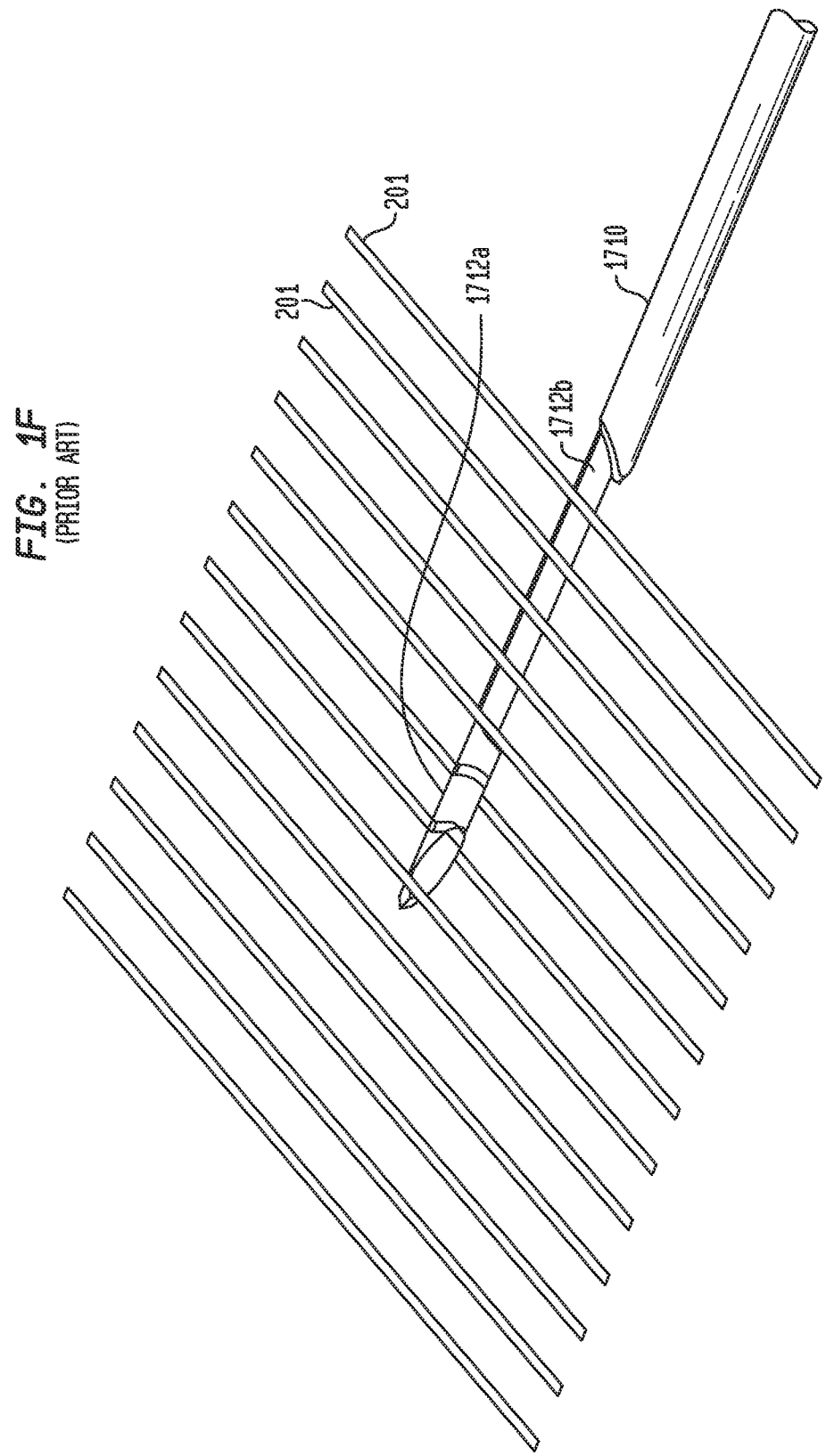
Figure 1H:
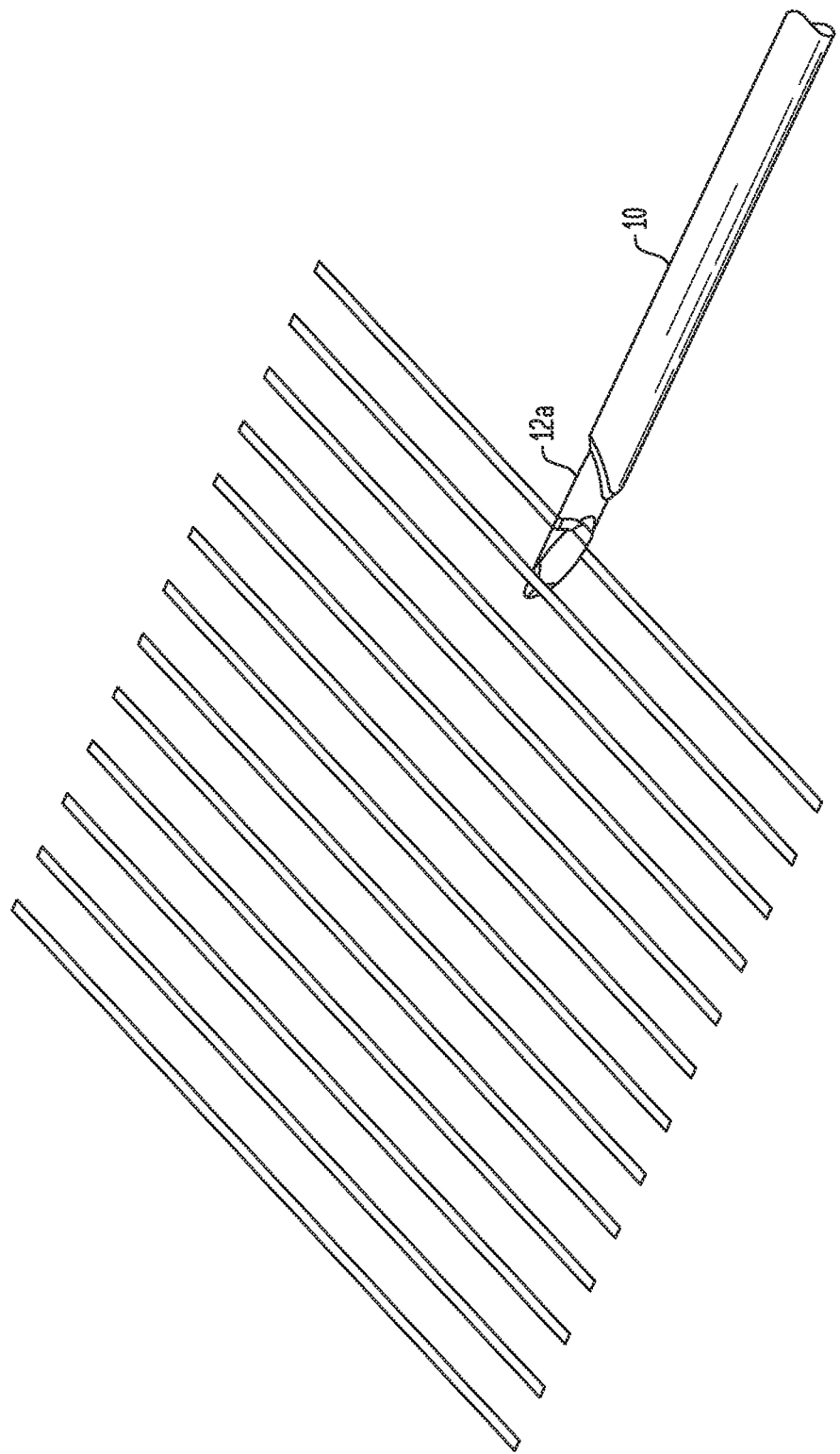

FIGS. 1e through 1g illustrate interaction between a known biopsy device and notional strand of tissue, and FIGS. 1h through 1i illustrate a like interaction using a core collector according to embodiments such as in FIG. 1a. FIG. 1e shows the sharp tip 1712a of a core collector 1712 protruding distally from a cannula 1710 (see FIG. 17a) and passing over one notional strand of tissue 200. At this stage, the view is like that of FIG. 1h, where tip 12a of core collector 12 protrudes distally from cannula 10 and passes under one notional strand or strip of tissue 200 and over the next strand 200. The difference from the known device starts being clearer by comparing FIG. 1f to FIG. 1i. In FIG. 1f, several notional strands of tissue are in notch 1712b of the core collector 1712 but are not held in place by the core collector. In contrast, in FIG. 1 every strand 200 is in a space between two adjacent teeth 12c or two adjacent teeth 12d of core collector 12 and thus is kept from distortion along the long axis of core collector 12. Comparing FIG. 1g with FIG. 1j shows that when the known core collector is fully extended distally from cannula 1710 all the strands 200 in notch 112a can slide axially, as seen in FIG. 1g, while in FIG. 1j each of the illustrated strands 200 in comparable positions are constrained from axial distortion due to teeth 12c and 12d.

Figure 1K:
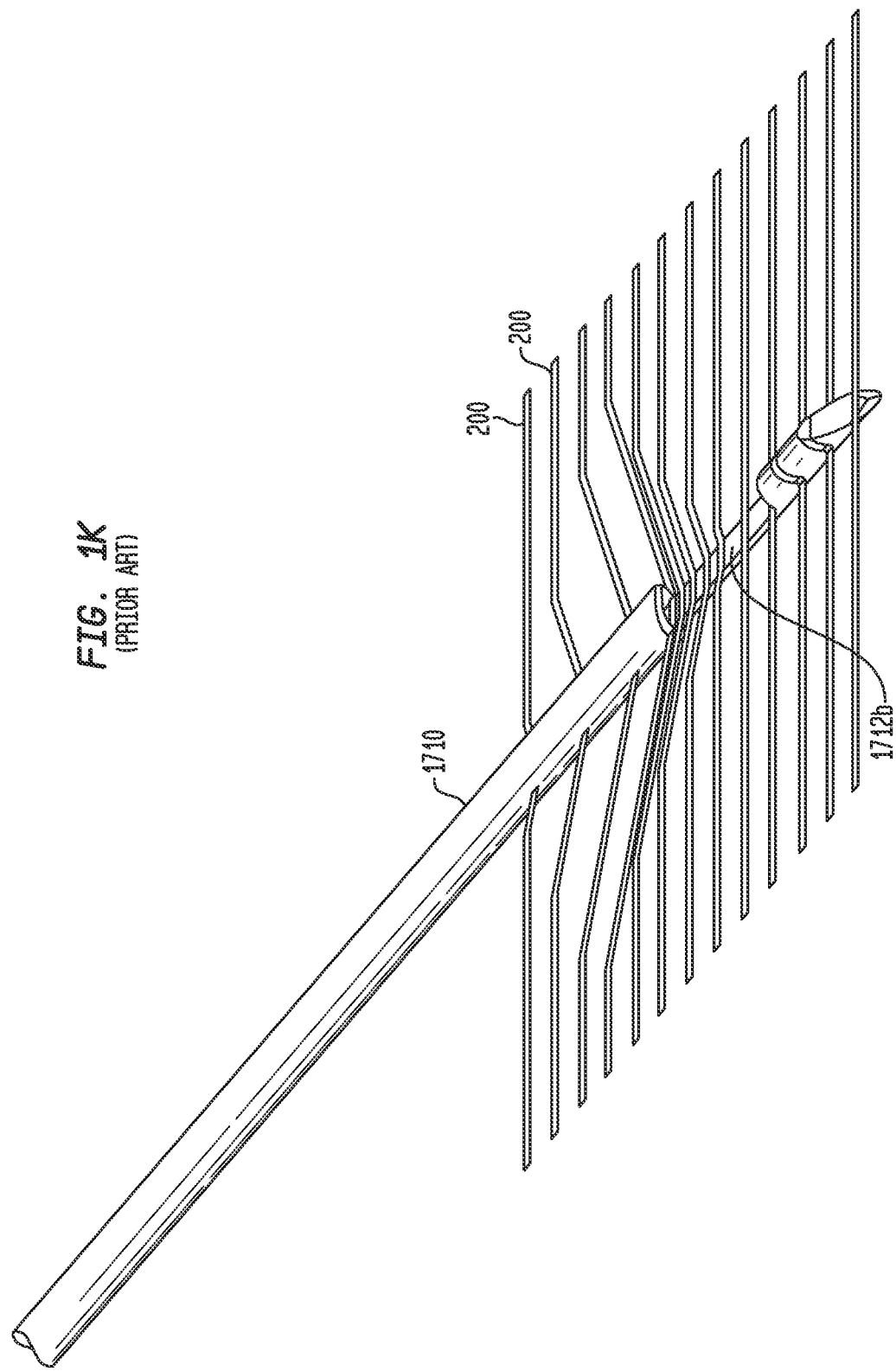

FIGS. 1l and 1k show specific benefits of constraining notional tissue strands 200 from motion distortion, compared with of allowing strand of tissue 200 to move along notch 1712b while cannula 1710 is moving distally over core collector 1712. FIGS. 1l and 1k show a known cannula 1710 in a midpoint of its distal motion over core collector 172, in which motion cannula 1710 severs tissue that has entered notch 1712b. As illustrates, the distal end of cannula 1710 tends to push notional tissue strands 200 distally as they are being severed, with the undesirable result of distorting the tissue sample held insider canula 1710. In addition, because the distal portion of core collector 1712 can bend up (in the orientation seen in FIGS. 1l and 1k), the space for a tissue sample in cannula 1710 diminishes. For these two reasons, the tissue sample can be distorted both in the axial and in the radial direction, reducing its clinical value.

In contrast, FIG. 1m illustrates how the new approach of core collector 12 maintains tissue sample integrity. Because tissue strands 200 are kept from axial motion relative to core collector 12, the distal cutting end of cannula 10 severs the essentially as they are in living tissue, reducing axial distortion. Moreover, because as explained above (see FIGS. 1c and 1d) the distal portion of core collector 12 is kept from bending bend and the free space 12e inside cannula 10 maintains its volume, radial distortion of the tissue sample inside cannula 10 is maintained. As a result, while with the known core collector-and-cannula combination the tissue sample can differ substantially from what it was in living tissue (it can be stretched, changing in diameter with position in the sample, and even broken in places), with the new approach described in this patent specification, tissue integrity can be substantially maintained and the clinical value of the tissue sample can be greatly enhanced.

Figure 2A:
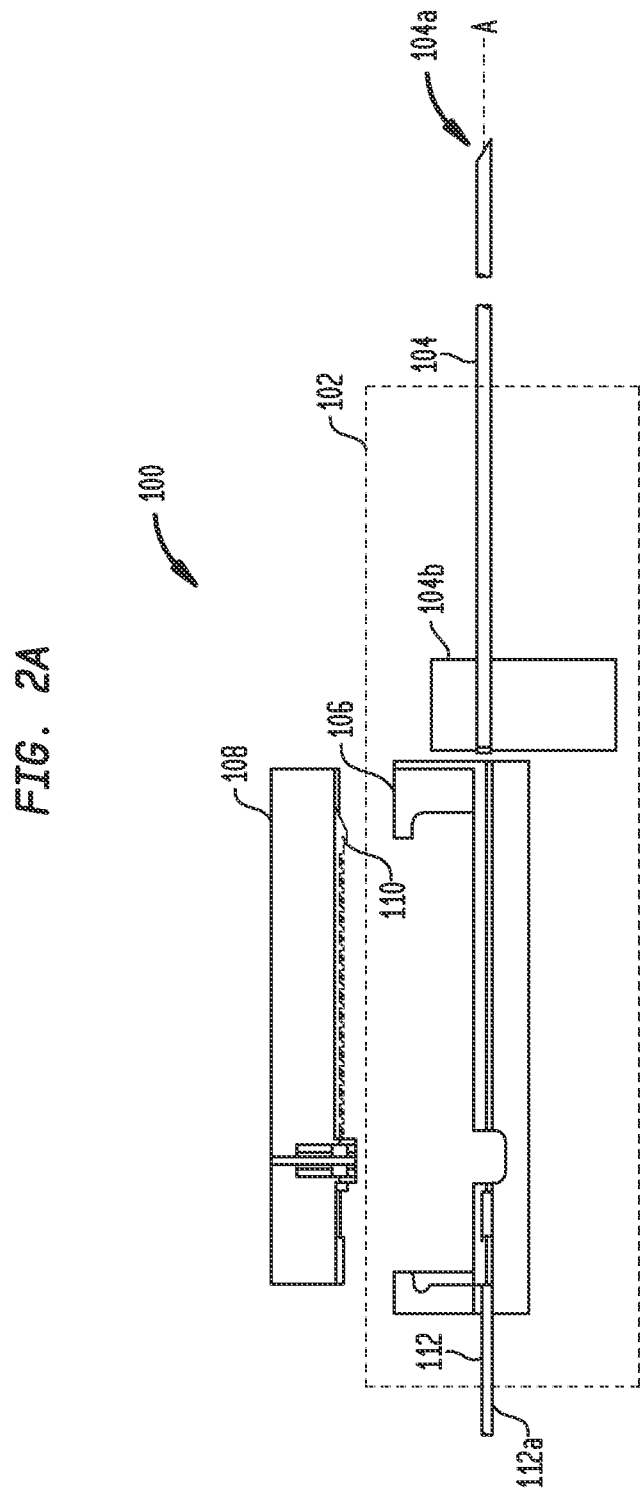
FIG. 2a is a partly schematic side view of a core biopsy instrument.

FIG. 2a illustrates a biopsy instrument that includes a cannula and a core collector that can be as illustrated in FIGS. 1a-1d or can use instead a core collector as illustrated in FIG. 2b. The instrument comprises a housing or handle 102 that is only schematically illustrated in FIG. 2a. As seen in FIG. 2a, a tubular cannula 104 extends distally and terminates in a sharp distal end 104a formed by cutting cannula 104 along a plane angled to a longitudinal central axis A. Cannula 104 has a proximal end held in a support block 104b that rides in a channel or along a guide rod or rods (not shown) inside handle 102 for motion along axis A both distally and proximally. A holder block 106 that is in a fixed position in handle 102 and is configured to releasably accept a cartridge 110 that holds a core collector 110. A drive rod 112 rides in a channel (not shown) in holder 106 that extends along central axis A, and a proximal portion 112a of drive rod 112 may extend proximally from a proximal end of handle 102 and may terminate proximally in a handle or knob (not shown) for manually moving rod 112 distally and proximally relative to handle 102. Drive rod 112 is constrained in handle 102 to move distally and proximally along central axis A.

Figure 2D:
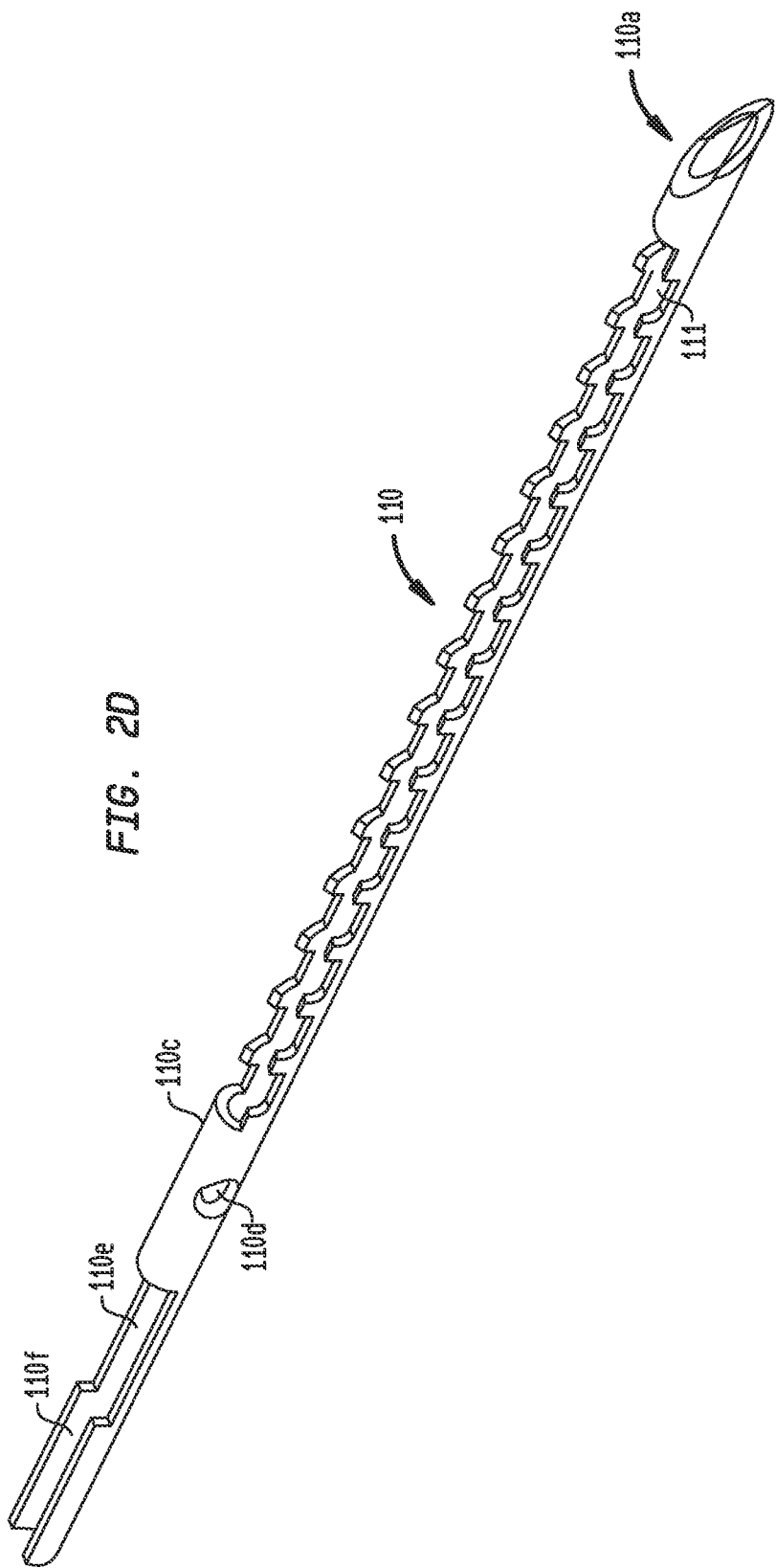

FIG. 2b is a side view of core collector 110 and FIGS. 2c-2e are different perspective views of the core collector according to some embodiments. Core collector 110 has a sharp distal end 110a that conforms to a plane angled to axis A and preferably is closed to no tissue would enter along axis A through that distal end. Two rows of teeth 110b1 and 110b2 extend proximally from distal end 110a of core collector 110. In cross-section normal to axis A, the portion of core collector 110 with the rows of teeth is roughly semicircular to define a trough 111 (FIGS. 2b-2e) with sidewalls from which teeth 110a and 110b extend. The teeth have proximal sides that can be inclined in the proximal direction and sharpened to serve an important function described further below. A tubular portion 110c of core collector 110 is proximal to the two rows of teeth and has side holes 110d that serve a function explained further below. A cutout 110e is proximal to tubular portion 110d and in cross-section normal to axis A is an arc that preferably extends over less than 180 degrees. The proximal end 110f of core collector 110 also is an arc but over a greater angle, preferably more than 180 degrees, so that cutout 110a ends in a step up proximally and distally formed by portions 110c and 110f.

FIGS. 3-6 are partly side views and partly sectional views of core biopsy instrument 100 that illustrate its operation in some embodiments. For clarity, handle 102 is omitted from these views but it is present when using the instrument. FIG. 3 illustrates an initial state, in which cartridge 108 has been releasably snapped into holder 106, such that core collector 110 is in a channel in holder 106 and is held in place, as described in more detail below, interlocked with a distal end of drive rod 112. FIG. 4 illustrates a state in which drive rod 112 has pushed core collector 110 distally such that its sharp distal end protrudes distally from cannula 104. For this purpose, drive rod 112 can be pushed distally manually from behind the proximal portion of handle 102. As discussed in more detail further below, the planes to which the distal ends of cannula 104 and core collector 110 conform are angled to central axis A in opposite directions. The distal end 110a of core collector 110 fits snugly in cannula 104 to keep tissue from entering space between them. In this state, a physician inserts cannula 104 and core collector 110 in a patient's tissue until the distal tip 110a of core collector 110 is at a desired position relative to the tissue to be sampled—for example, just outside the patient's prostate or just inside the prostate, or up to or just into a suspected lesion. This desired position can be determined based on clinical experience or by feel or by using imaging devices such as an ultrasound probe that can but need not be attached to instrument 100 or by use of other imaging modalities. FIG. 5 illustrates a state in which core collector 110 has been advanced distally relative to cannula 104 such that all or at least some of the two rows of teeth are distal from the distal tip of cannula 104. For this purpose, drive rod 112 can be spring loaded as discussed further below such that releasing the spring action drives rod 112 distally, thus pushing core collector 110 out of cannula 104 over a desired distance that can be set by a suitable stop (not shown) for drive rod 112 in handle 102. In this state, core collector 110 has penetrated the tissue to be sampled (not shown) and a sample of tissue has entered trough 111. The angle of the plane to which the sharp distal end 110a of core collector 110 conforms helps drive tissue in trough 111 because driving the distal end 110a of core collector 110 into tissue compresses tissue that is on the open side of trough 111 (down as viewed in FIG. 5) and this compressed tissue tends to spring back up into trough 111. FIG. 6 illustrates a state reached shortly (preferably less than a second) after core collector 110 has been advanced distally to the state of FIG. 5. To reach the state of FIG. 6, cannula 104 also preferably is spring-loaded such that its spring action is released shortly after the spring action for core collector 110 is released, to drive cannula 104 distally over core collector 110. This distal motion of cannula 104 cuts from surrounding tissue the sample of tissue that has entered a trough 111 of core collector 110. In this cutting action, the two rows of teeth help keep the tissue sample from bunching up or exiting trough 111 as described in more detail further below. Thereafter, both cannula 104 and core collector 110, in their respective positions seen in FIG. 6, are pulled proximally, for example by manually pulling proximally drive rod 112 and holder block 106 holding cannula 104, until cannula 104 and core collector 110 are in the positions seen in FIG. 4, and drive rod 112 is pulled further proximally until it brings core collector 110 to the position seen in FIG. 3. Then, cartridge 108, which has gripped core collector 110 (with the tissue sample therein) as described further below, is manually pulled away from handle 102, and processed chemically and sealed, for example for sending to a laboratory. Notably, the tissue sample remains in cartridge 108 and remains undisturbed by handling. The orientation of the tissue sample relative to the living tissue from which the sample was extracted also is preserved due to core collector remaining in cartridge 106, as the distal end of cartridge 106 is known, so the laboratory would have an unambiguous indication or which end of the tissue sample is distal and which is proximal.

FIG. 7 is a partial side view of a distal portion of core collector 110 and a sectional view of a distal position of cannula 104 and FIG. 8 is a perspective view of the same portions of cannula 104 and core collector 110. As seen in FIG. 7, the distal end 110a of core collector 110 conforms to a plane B that is inclined in one direction to central axis A and the distal end 104a of cannula 104 conforms to a plane C inclined in an opposite direction to central axis A. As seen in FIGS. 7 and 8, distal end 104a of cannula 104 is sharpened by gradually reducing the thickness of its wall in the distal direction until it reaches the inside diameter of cannula 104.

FIG. 9 is a perspective view of cartridge 108 and FIG. 10 is a perspective view of a portion of the cartridge as seen from a different viewpoint according to some embodiments. Cartridge 108 comprises a channel 108a that extends along central axis A and is dimensioned to snugly receive core collector 110 but allow it to move distally and proximally in the channel. A proximal portion of cartridge 108 has a cage 108b with openings through which core collector 110 passes and two pins 108c that are resilient and pinch into holes 110d (FIGS. 2a-2d) of core collector 110 when the core collector is in cartridge 108 in the position seen in FIGS. 9 and 10. Pins 108c are sufficiently resilient to allow drive rod 112 to push core collector 110 distally out of engagement with pins 108c and also to allow drive rod 112 to pull core collector 110 proximally to the position seen in FIGS. 9 and 10, at which pins 108a can again grip the core collector and keep it in place while cartridge 108 is pulled out of handle 102. Cartridge 108 has provisions such as a cantilevered projection 108d to releasably snap into secure engagement with corresponding projections or indentations (not shown) in handle 102.

Figure 11:
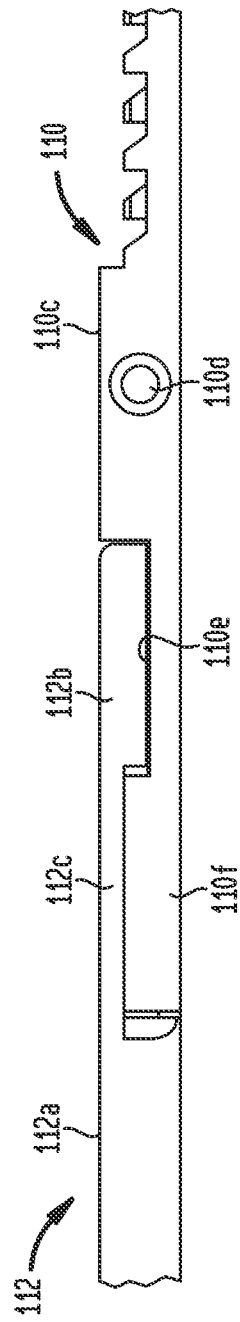
FIG. 11 is a side view of a drive rod interlocked with a proximal portion of a core collector according to some embodiments.

FIG. 11 is a side view illustrating an interlock of drive rod 112 and core collector 110 and FIG. 12 is a perspective view of the proximal end of core collector 110 and the distal end of drive rod 112 according to some embodiments. Drive rod 112 has a thicker distal end 112b that fits in the smaller-arc cutout 110e of core collector 110 and a thinner portion 112c immediately proximal that fits into the larger-arc cutout 110f in core collector 110. In operation, the distal end of drive rod 112 is in its position seen in FIG. 2a when cartridge 108 is not yet inserted in handle 102. Inserting cartridge 108 to the position seen in FIG. 3 places drive rod 112 and core collector 110 in the interlocked position seen in FIG. 11. Removing cartridge 108 by pulling it from handle 102 disengages core collector 110 from interlock with drive rod 112 while drive rod 112 remains in place in handle 102.

Figure 13D:
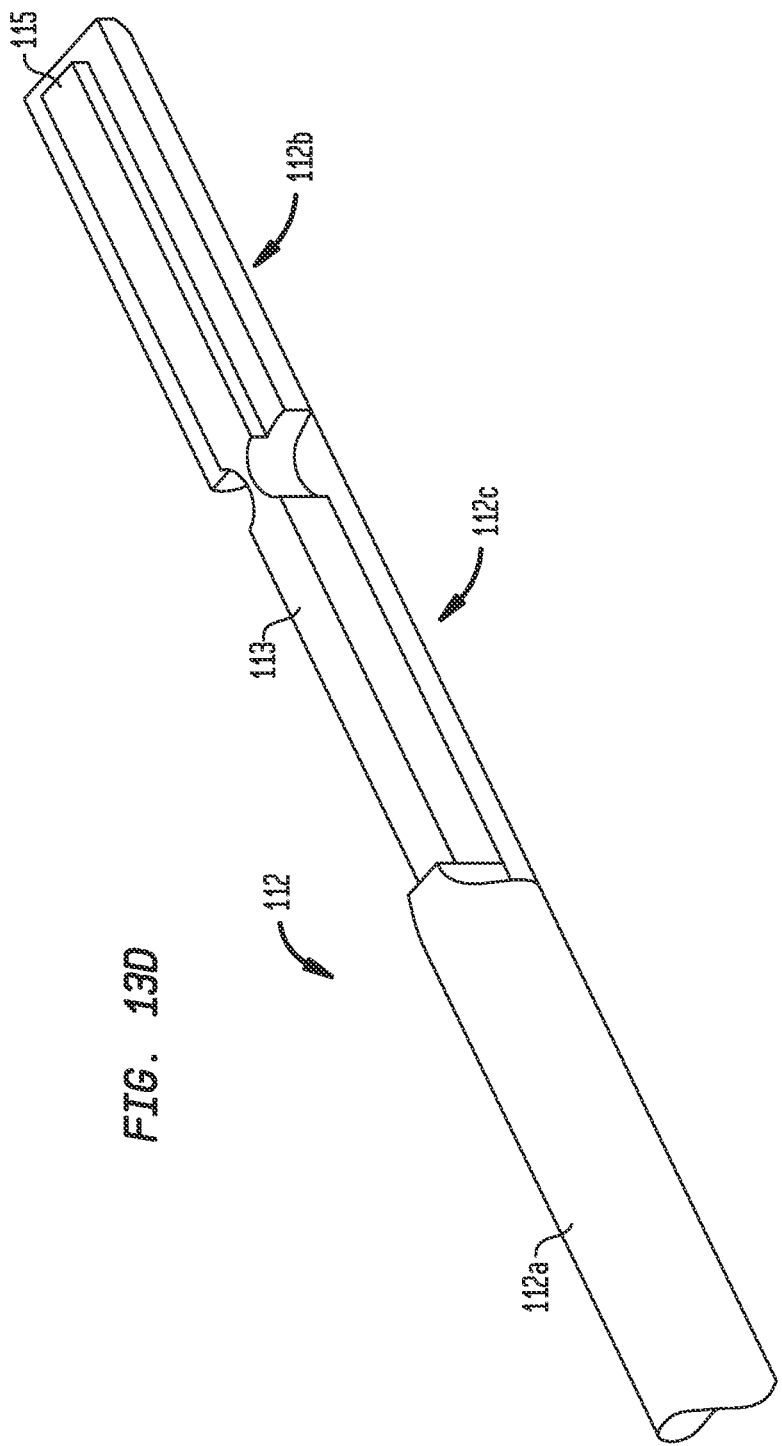

FIG. 13a is a side view of a distal portion of drive rod 112, FIG. 13b is a plan view, and FIGS. 13c and 13d are two different perspective views. Portion 112c of drive rod 112 comprises a thinner band on one side of a stiffening rib 113, and portion 112b comprises a wider arc and a thinner rib 115, all serving to provide an interlock with core collector 110.

Figure 14A:
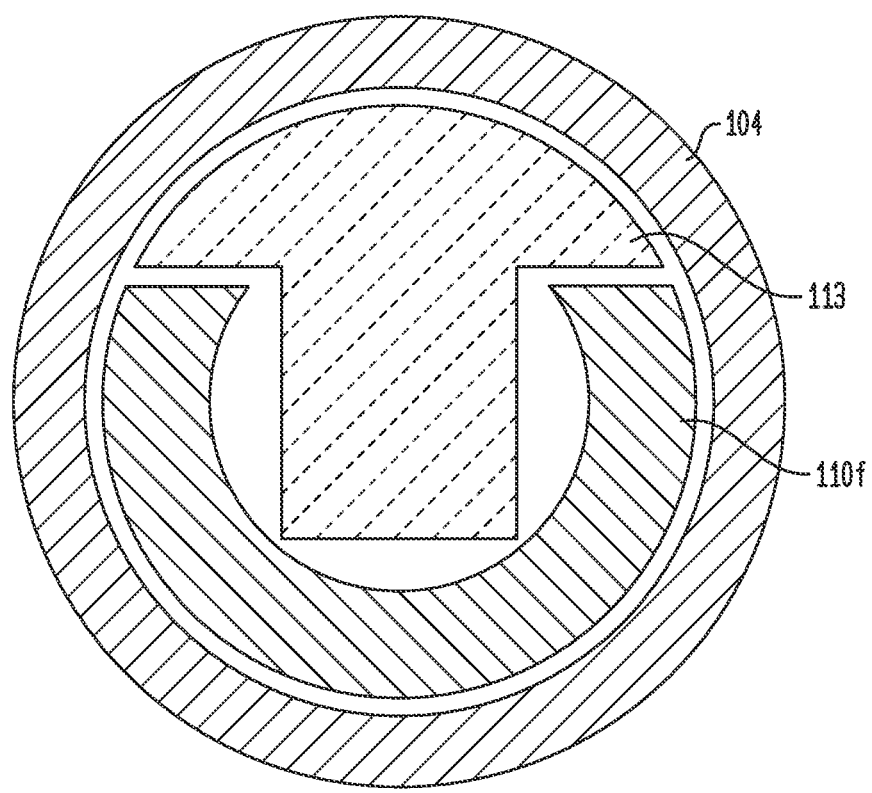
FIGS. 14a and 14b are sectional views along planes D and E respectively of FIG. 4, and FIGS. 14c-14e are sectional views along planes F-H respectively of FIG. 7.
Figure 14B:
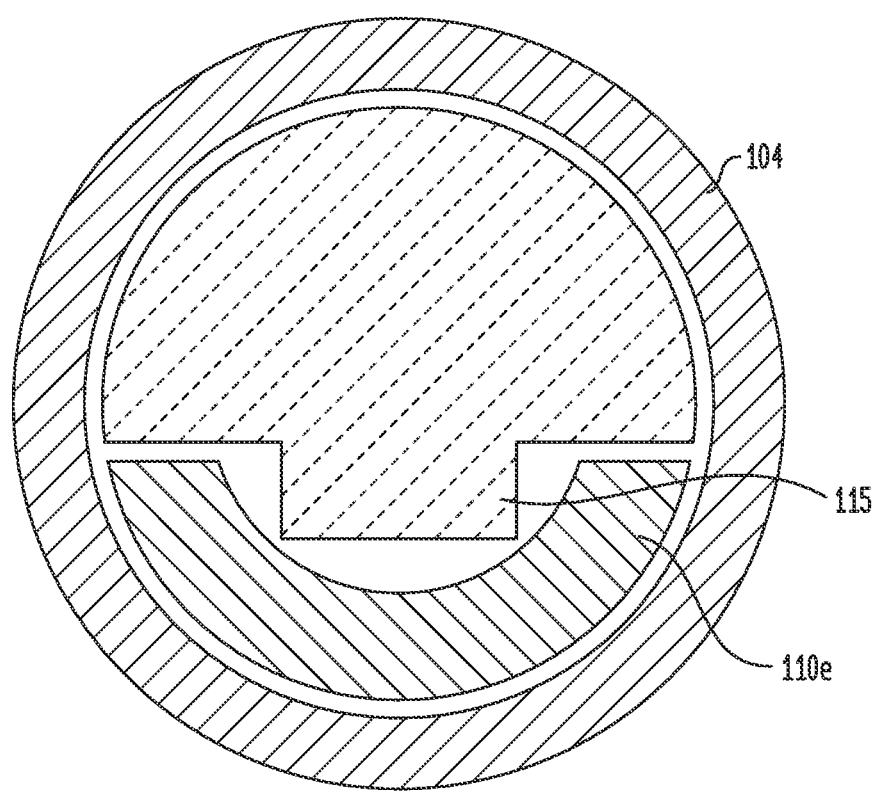
Figure 14C:
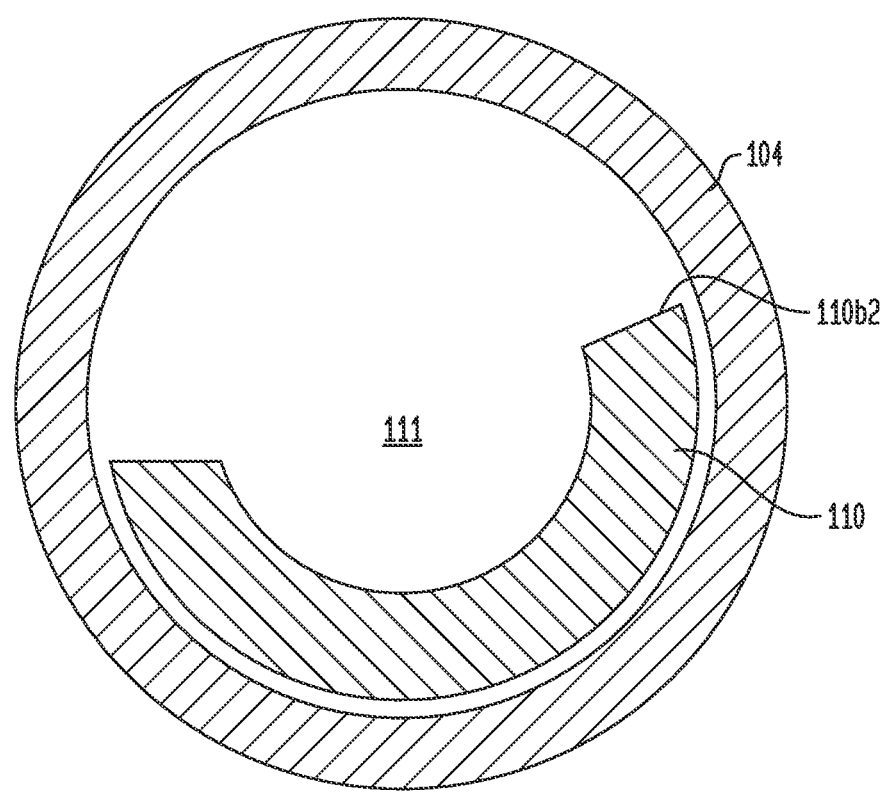
Figure 14D:
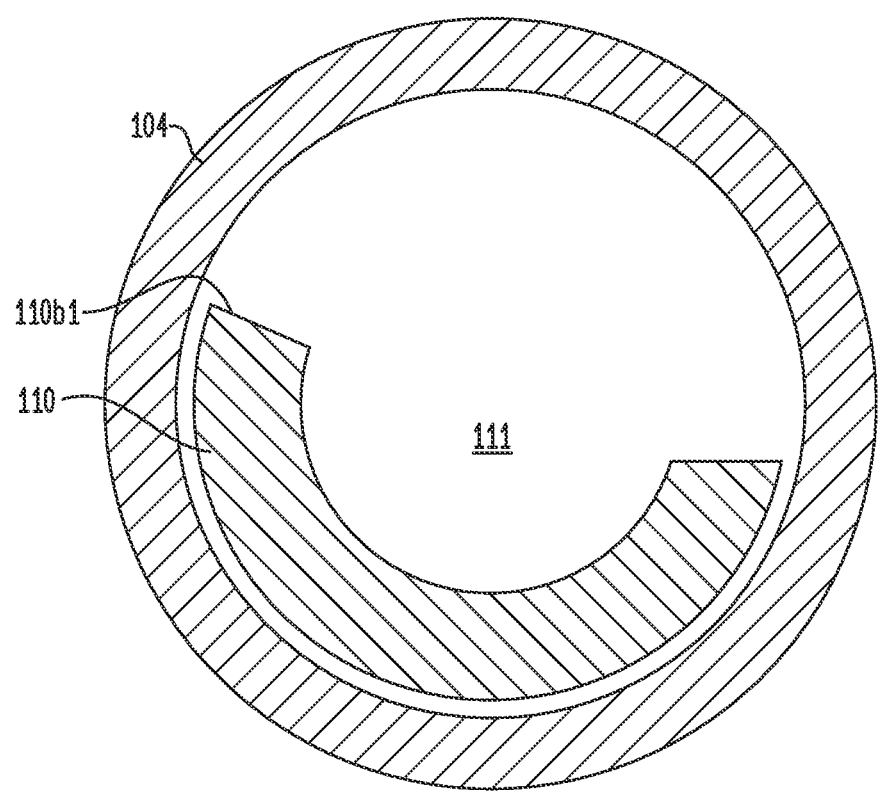
Figure 14E:
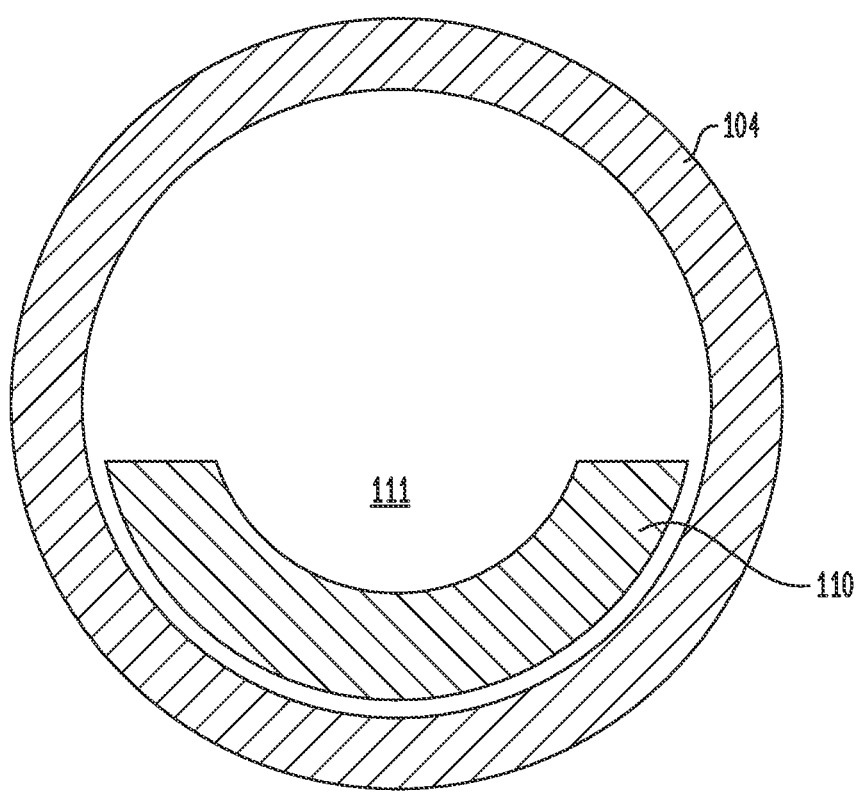

FIGS. 14a-14e illustrate cross-section of core collector 110 inside cannula 104 at respective planes normal to central axis A. FIG. 14a is a section along plane D in FIG. 4 and illustrates how stiffening rib 113 (FIGS. 13b-13d) fits in portion 110f (FIG. 12) of core collector 110 when surrounded by cannula 104 in the state shown in FIG. 12. FIG. 14b is a section along plane E of FIG. 4 and illustrates how rib 115 (FIGS. 13b-13d) fits in portion 110f (FIG. 12) of core collector 110 that is in canula 104 in the state shown in FIG. 12. FIG. 14c illustrates a section along plane G in FIG. 7, and shows a tooth 110b2 at right (as viewed in FIG. 14c) that extends above the left sidewall of trough 111 of core collector 110 in that section. FIG. 14d illustrates a section along plane F in FIG. 7 showing a tooth 110b1 at left (as viewed in FIG. 14d) that extends above the right sidewall of core collector 110 in that section. FIG. 14e illustrates a section along plane H in FIG. 7, where there are no teeth and shows both sidewalls of trough 111 at same height.

Notably, as seen for example in FIGS. 7 and 8, the two rows of teeth are staggered relative to each other—where in a cross-section normal to central axis A there is a tooth 110b1 but no tooth 110b2 and where there is a tooth 110b2 there is no tooth 110b1. This can facilitate tissue enter, and stay in, trough 111 compared a trough extending over an arc like that of arcs of FIGS. 14c and 14d but lacking teeth.

In addition, as seen for example in FIG. 8, the distal sides of the teeth can be inclined in the proximal direction, and in some embodiments the proximal sides of the teeth also can be somewhat inclined in the proximal direction. In other embodiments, the proximal sides of the teeth need not be inclined in the proximal direction or can be inclined in a different direction.

Notably, the teeth can be cut such that they have sharp edges on their proximal sides. Having the distal sides of the teeth inclined reduces the portion of a sidewall of trough 111 that is occupied by teeth and thus facilitates entry of tissue in the trough. Having the proximal sides of the teeth inclined in the proximal direction and/or formed with sharp edges facilitates severing of the tissue sample in trough 111 as cannula 104 moves distally over core collector 110.

Figure 15:
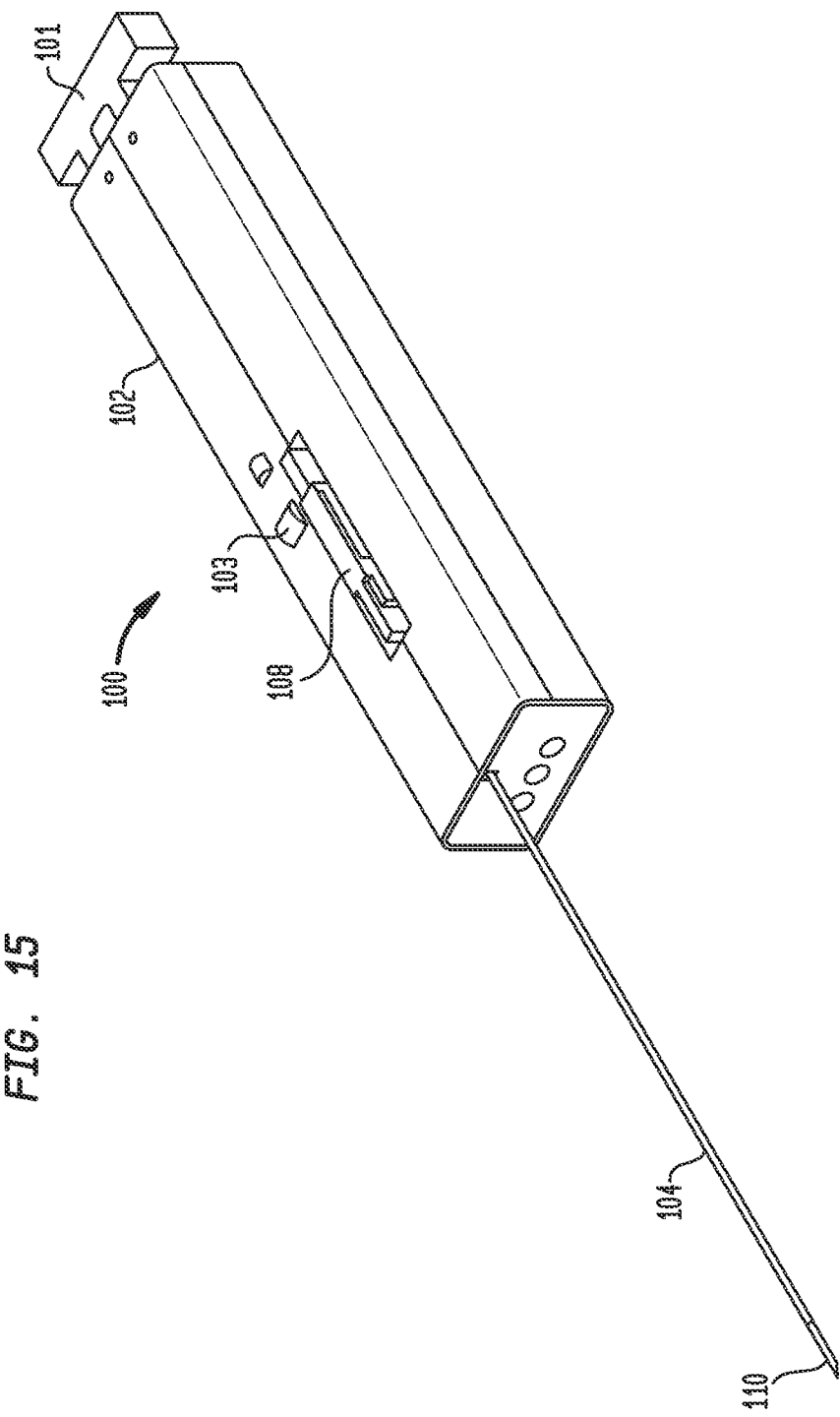
FIG. 15 is a perspective view of a core biopsy instrument according to some embodiments.

FIG. 15 is a perspective view of a core biopsy instrument 100 that shows an example of a handle 102, cannula 104 and a distal portion of core collector 110 protruding distally from cannula 104. FIG. 15 illustrates a knob 101 at the proximate side of handle that is affixed to the proximal end of drive rod 112 to manually pull the rod proximally and push it distally as needed. In addition, knob 101 can be connected to springs (not shown) in handle 102 to compress them when knob 101 is pulled proximally until the springs latch in a compressed state. These springs when released drive distally core collector 110 and cannula 104 as described above. FIG. 15 also shows a manually operated switch 103 that when pressed releases from a latched state the compressed spring that drives rod 112 distally. The spring the drives cannula 104 distally can be released by a delay actuated by forward motion of rod 112 when driven by the spring releases by actuating switch 103. In a specific and non-limiting example, the approximate dimensions of handle 102 are: length 9.0 inches, width 2.2 inches, and height 1.3 inches. In this example, cannula 104 protrudes distally from handle 102 approximately 6 inches.

In one mode of operation, cannula 104 can be withdrawn from the patient after instrument 100 has reached the state illustrated in FIG. 6 or has reverted to the state of FIG. 4 after having reached the state of FIG. 6. For another tissue sample, the same instrument or an unused duplicate can be used as described above to take another tissue sample. Alternatively, after reaching the state of FIG. 6 or after reverting to the state of FIG. 4, cannula 104 can be left in the patient or moved to a new orientation and/or depth in the patient, and only core collector 110 can be withdrawn into cartridge 108, the cartridge can be removed from handle 102 and replaced with a new cartridge, with a new core collector, and the procedure discussed above can be repeated to take a new tissue sample. Cartridges can be removed and replaced plural times while cannula 104 remains in the patient to thereby take multiple samples of tissue.

FIGS. 16a-16d illustrate a sequence of operation of spring-loaded drives for cannula 104 and core collector 110 according to some embodiments. For clarity, handle 102 is omitted but it encloses the illustrated components except for the portions of cannula 104 and core collector 110 that protrude distally from the handle and except for the portion of drive rod 112 that extend proximally of the handle. FIG. 16a shows a spring 122 held compressed between a block 120 affixed to handle 102 and a block 112d that is affixed to drive rod 112 and can move distally and proximally along the central axis. A latch 118 holds spring 122 compressed in the position of FIG. 16a. FIG. 16b shows spring 122 released by pivoting latch 118 and expanding distally. Latch 118 can be released by operating a manual trigger, for example trigger 103 (FIG. 15). FIG. 16c shows spring 122 fully expanded, to a position in which block 112d has bumped the proximal end of latch 116 and has caused latch 116 to pivot to the position seen in FIG. 16c and has released spring 124 to drive block 104b and thus cannula 104 distally. A desired delay (not shown) such as a mechanical damper or buffer can be introduced between block 112d and the proximal end of latch 116 if it is desired to increase the time between core needle 110 reaching the end of its distal motion and the start of the distal motion of cannula 104. FIG. 16d shows the positions of the illustrated components after cannula 104 and core collector 110 have reached the end of their distal motions Although the foregoing has been described in some detail for purposes of clarity, it will be apparent that certain changes and modifications may be made without departing from the principles thereof. There can be many alternative ways of implementing both the processes and apparatuses described herein. Accordingly, the present embodiments are to be considered as illustrative and not restrictive, and the body of work described herein is not to be limited to the details given herein, which may be modified within the scope and equivalents of the appended claims.

The invention claimed is:

1. A biopsy instrument comprising:
    a tubular cannula that extends along a longitudinal axis and has an inside wall and a sharp distal end;
    a core collector that fits in the cannula for motion relative thereto inside the cannula along said axis and has a sharp distal tip and a cradle portion extending proximally from the sharp tip along said axis;
    wherein said cannula and core collector are configured to move linearly relative to each other along said axis between (i) a first relative position in which the cannula is proximal from at least a portion of said cradle portion and said cradle portion protrudes distally from the cannula, for a tissue sample to enter said cradle portion, and (ii) a second relative position in which said cannula has moved distally relative to said core collector to thereby sever said tissue sample from surrounding tissue and said cradle portion is surrounded by the cannula;
    wherein said cradle portion of the core collector has a convex bottom surface and an upper surface with side walls forming said cradle portion;
    wherein said side walls of the core collector in an axial view extend over a sufficiently large arc to keep the core collector centered in the cannula to keep the bottom surface of the core collector against the inside wall of the cannula, and to thereby resist bending or deflection of a portion of the core collector that extends distally from the cannula during linear relative movement of the cannula and core collector both from the first to the second and from the second to the first relative positions thereof;
    wherein said side walls of the core collector comprise rows of teeth, with the teeth of each of said rows spaced from each other along said axis; and
    wherein said teeth are configured to engage tissue that has entered said cradle portion while the core collector is protruding distally from the cannula in said first relative position and, as the cannula moves distally over the cradle to the second relative position, to keep said tissue from distorting as the cannula severs a tissue sample from surrounding tissue, thereby maintaining structural integrity of the tissue sample along said axis.

2. The biopsy instrument of claim 1, in which said teeth are configured to engage said tissue to keep the tissue sample from compressing and stretching along said axis as the sample is being severed from surrounding tissue by the cannula moving over the cradle portion along said axis.

3. The biopsy instrument of claim 2, in which:
    the teeth of each of said side walls are spaced axially from each other by flat portions and are staggered relative to those of the other side wall such that some cross-sections contain teeth of both rows, some contain only a tooth of one of the rows, and some contain no teeth; and
    in said cross-sections that contain teeth of both rows, the cradle portion's circumference is approximately half a circle;
    thereby providing a cutting action as the cannula moves over the cradle that facilitates maintaining structural integrity of the sample before being severed from surrounding tissue.

4. The biopsy instrument of claim 1, in which said core collector is configured to move linearly along said axis to said first position from an initial position in which said cradle portion of the core collector is inside said cannula.

5. The biopsy instrument of claim 1, in which in an axial view from a distal to a proximal end of the cradle portion, the cradle portion extends to approximately a half-circle.

6. The biopsy instrument of claim 1, in which at least some cross-sections of the cradle portion contain teeth of only one of said rows of teeth.

7. The biopsy instrument of claim 1, in which at least some cross-sections of said cradle portion are entirely free of said teeth.

8. A biopsy instrument comprising:
    a tubular cannula that extends along a central longitudinal axis and has an inside wall and a sharpened distal end;
    a core collector that that fits in said cannula for linear motion relative thereto along said central longitudinal axis and has a sharp distal tip and a cradle portion extending along said axis proximally from the sharp distal tip;
    wherein said cannula and core collector are configured to move linearly relative to each other along said central longitudinal axis between (i) a first relative position in which said cradle portion protrudes distally from the cannula for a tissue sample to enter said cradle portion and (ii) a second relative position in which said cannula and core collector have moved distally relative to each other to thereby sever said tissue sample in the cradle portion from surrounding tissue;
    wherein said cradle portion of the core collector is elongated along said central longitudinal said axis and has a convex bottom and an upper surface with side walls forming said cradle portion;
    wherein said side walls of the core collector extend above a mid-plane of said inside wall that coincides with said central longitudinal axis and comprise rows of teeth, with the teeth of each of said rows spaced from each other along said central longitudinal axis such that cross-sections of the cradle portion contain teeth of both rows, or contain only a tooth of one of the rows, or are entirely free of said teeth; and
    wherein said teeth are configured to engage tissue that has entered said cradle portion while the core collector is protruding distally from the cannula and thereby keep said tissue from distorting as the cannula and cradle portion move from the first to the second relative position thereof to thereby sever a tissue sample from surrounding tissue, thereby maintaining structural integrity of said tissue sample.

9. The biopsy instrument of claim 8, in which said teeth are configured to maintain structural integrity of the tissue sample along said axis.

10. The biopsy instrument of claim 8, in which said teeth are configured to maintain structural integrity of the tissue sample in a direction across said central longitudinal axis.

11. The biopsy instrument of claim 8, in which said teeth are configured to maintain structural integrity of the tissue sample both along said central longitudinal axis and in a direction across said central longitudinal axis.

12. A biopsy instrument comprising:
    an axially extending tubular cannula that has an inside wall and a sharp distal end;
    an axially extending core collector that has a sharp distal tip and a proximal portion extending proximally from the sharp tip and configured to fit in the cannula for linear relative motion between the cannula and the core collector;
    wherein said proximal portion of the core collector has a convex bottom and an upper surface with lateral teeth along at least a portion of the axial length of the core collector, forming a cradle portion that in an axial view from a distal toward a proximal end thereof extends over a sufficiently large arc angle to keep said proximal portion of the core collector radially centered in said cannula and said convex bottom against the inside wall of the cannula by said lateral teeth bearing against said inside wall of the cannula, thereby providing an open space for a tissue sample;

wherein said lateral teeth comprise two laterally spaced rows of teeth and wherein the teeth of each row are axially spaced from each other; and wherein said relative motion between the cannula and the core collector comprises motion along said axis between (i) a first relative position in which said proximal portion of the core collector protrudes distally from the cannula for a tissue sample to enter therein and (ii) a second relative position in which said cannula has moved distally relative to said core collector to thereby sever said tissue sample from surrounding tissue and said proximal portion of the core collector with the core sample therein is inside said cannula.

13. The biopsy instrument of claim 12, in which said bottom of the proximal portion of the core collector includes one or more sections normal to said axis that form axial spaces of said cradle free of said teeth and each of said sections has a circumference that extends over less than half the circumference of the cannula's inside wall.

14. The biopsy instrument of claim 12, in which said teeth in each of said rows are axially spaced from each other by flat spaces and are polished smooth.

15. The biopsy instrument of claim 12, in which said proximal portion of said core collector is machined from a solid rod.

16. The biopsy instrument of claim 12, further including a driving mechanism engaging proximal ends of the cannula and core collector to selectively drive distally first the core collector so that said proximal portion of the core collector protrudes distally from the cannula by a selected distance and then the cannula so that the sharpened distal end of the cannula advances to said sharp distal end of the core collector to cut a tissue sample extending in said open space of the core collector while maintaining structural integrity of the tissue sample.

17. The biopsy instrument of claim 12, in which said core collector is configured to move linearly along said axis to said first position from an initial position in which said cradle portion of the core collector is inside said cannula.

18. A method comprising:
providing an axially extending core collector with a distal portion that comprises two rows of teeth formed at lateral sides of the core collector to form a cradle portion between the two rows of teeth, with the teeth of each row axially spaced from each other;

providing a cannula configured to surround the core collector for relative axial motions between the cannula and core collector between (i) a first relative position in which the cradle portion protrudes distally from the cannula and (ii) a second relative position in which the cradle portion is inside the cannula, wherein the cradle portion in an axial view from a distal to a proximal end thereof extends over an arc angle sufficient to keep the core collector radially centered in the cannula by the lateral sides and a bottom of said cradle portion bearing against the inside of the cannula during said motions both from the first to the second and from the second to the first relative positions;

introducing the cannula and core collector into tissue and driving a selected length of the core collector distally from the cannula and into tissue;

thereafter, driving the cannula distally over said core collector to thereby sever a sample of said tissue while keeping the core collector radially centered in said cannula; and extracting a tissue sample collected in an open space between the cannula and the cradle portion formed between the two rows of teeth of the core collector.

19. The method of claim 18, further comprising:
driving the core collector with said tissue sample therein proximally to a position aligned with a cartridge that is releasably secured to a handle supporting a proximal portion of the cannula and core collector and releasably latching the core collector to the cartridge; and removing the cartridge with the core collector latched thereto from said handle.

20. The method of claim 18, further comprising extracting a tissue sample with structural integrity from said core collector.

21. A biopsy instrument comprising:
an axially extending core collector that has a convex underside and an upper surface;

wherein said core collector comprises two axially extending rows of teeth formed at lateral sides of the core collector and forming a cradle portion between them, with the teeth of each row axially spaced from each other; and a tubular cannula having an inside wall and a sharp distal end;

wherein the cannula is configured to receive therein the core collector for relative linear motion between (i) a first relative position in which a selected length of the core collector extends distally from the cannula and (ii) a second position in which the cannula has moved distally over and relative to the core collector from said first position;

wherein in an axial view from a distal toward a proximal end of the cradle portion of the core collector, the cradle portion extends over an arc angle sufficient to keep the core collector radially centered in the cannula due to the lateral sides of the cradle portion bearing against the inside wall of the cannula to thereby keep the convex underside of the core collector from moving away from the cannula inside due to forces acting on the core collector in a direction transverse to the axial length of the core collector both during said motion from the first to the second positions and during said motion from the second to the first positions.

22. The biopsy instrument of claim 21, in which said cradle portion has cross-sections some of which include a tooth of only one of said rows, and some of which include none of said teeth, wherein axial lengths of the cradle portion that in cross-section include one tooth are flanked by at least one cross-section that includes no teeth.

23. The biopsy instrument of claim 21, in which the arc over which the cradle portion extends in said axial view is approximately a half-circle.

* * * * *